(12) United States Patent
Gerber et al.

(10) Patent No.: US 11,045,790 B2
(45) Date of Patent: *Jun. 29, 2021

(54) STACKED SORBENT ASSEMBLY

(71) Applicant: Medtronic, Inc., Minneapolis, MN (US)

(72) Inventors: Martin T. Gerber, Maple Grove, MN (US); Christopher M. Hobot, Rogers, MN (US)

(73) Assignee: Medtronic, Inc., Minneapolis, MN (US)

( * ) Notice: Subject to any disclaimer, the term of this patent is extended or adjusted under 35 U.S.C. 154(b) by 8 days.

This patent is subject to a terminal disclaimer.

(21) Appl. No.: 16/435,772

(22) Filed: Jun. 10, 2019

(65) Prior Publication Data

US 2019/0291079 A1     Sep. 26, 2019

Related U.S. Application Data

(63) Continuation of application No. 14/645,394, filed on Mar. 11, 2015, now Pat. No. 10,357,757.

(60) Provisional application No. 62/016,611, filed on Jun. 24, 2014.

(51) Int. Cl.
| | | |
|---|---|---|
| *B01J 20/28* | (2006.01) | |
| *B01J 20/22* | (2006.01) | |
| *B01J 20/02* | (2006.01) | |
| *A61M 1/16* | (2006.01) | |
| *B01J 20/06* | (2006.01) | |
| *B01J 20/20* | (2006.01) | |

(52) U.S. Cl.
CPC ...... *B01J 20/28052* (2013.01); *A61M 1/1696* (2013.01); *B01J 20/0211* (2013.01); *B01J 20/06* (2013.01); *B01J 20/20* (2013.01); *B01J 20/22* (2013.01); *B01J 2220/66* (2013.01)

(58) Field of Classification Search
CPC .. B01J 20/28052; B01J 20/20; B01J 20/0211; B01J 20/06; B01J 20/22; B01J 2220/66; A61M 1/1696

See application file for complete search history.

(56) References Cited

U.S. PATENT DOCUMENTS

| | | | |
|---|---|---|---|
| 1,617,288 | A | 2/1927 | Kenney |
| 2,703,313 | A | 1/1950 | Gill |
| 3,608,729 | A | 9/1971 | Haselden |
| 3,617,545 | A | 11/1971 | Dubois |

(Continued)

FOREIGN PATENT DOCUMENTS

| | | |
|---|---|---|
| CN | 1487853 A | 4/2004 |
| CN | 102573618 | 7/2012 |

(Continued)

OTHER PUBLICATIONS

U.S. Appl. No. 13/100,847, filed Nov. 10, 2011, C-Tech BioMedical Inc.

(Continued)

*Primary Examiner* — Waqaas Ali

(57) ABSTRACT

A stacked sorbent assembly for use in sorbent dialysis. The stacked sorbent assembly contains two or more interchangeable sorbent pouches that allow for fluid to freely pass into and through the sorbent materials, while keeping the sorbent materials inside the sorbent pouches. Any of the pouches in the sorbent cartridge can be reused and/or recharged.

19 Claims, 12 Drawing Sheets

(56) References Cited

U.S. PATENT DOCUMENTS

| | | | |
|---|---|---|---|
| 3,617,558 | A | 11/1971 | Jones |
| 3,669,878 | A | 6/1972 | Marantz |
| 3,669,880 | A | 6/1972 | Marantz |
| 3,776,819 | A | 12/1973 | Smith |
| 3,840,835 | A | 10/1974 | Kussy |
| 3,850,835 | A | 11/1974 | Marantz |
| 3,884,808 | A | 5/1975 | Scott |
| 3,902,490 | A | 9/1975 | Jacobsen et al. |
| 3,989,622 | A | 11/1976 | Marantz |
| 4,000,072 | A * | 12/1976 | Sato .................... A61M 1/1696 210/315 |
| 4,060,485 | A | 11/1977 | Eaton |
| 4,073,725 | A | 2/1978 | Takeuchi |
| 4,094,775 | A | 6/1978 | Mueller |
| 4,142,845 | A | 3/1979 | Lepp |
| 4,192,748 | A | 3/1980 | Hyden |
| 4,206,054 | A | 6/1980 | Moore |
| 4,209,392 | A | 6/1980 | Wallace |
| 4,269,708 | A | 5/1981 | Bonomini |
| 4,371,385 | A | 2/1983 | Johnson |
| 4,374,382 | A | 2/1983 | Markowitz |
| 4,376,707 | A | 3/1983 | Lehmann |
| 4,381,999 | A | 5/1983 | Boucher |
| 4,460,555 | A | 7/1984 | Thompson |
| 4,556,063 | A | 12/1985 | Thompson |
| 4,562,751 | A | 1/1986 | Nason |
| 4,581,141 | A | 4/1986 | Ash |
| 4,612,122 | A | 9/1986 | Ambrus |
| 4,650,587 | A | 3/1987 | Polak |
| 4,661,246 | A | 4/1987 | Ash |
| 4,678,408 | A | 7/1987 | Mason |
| 4,684,460 | A | 8/1987 | Issautier |
| 4,685,903 | A | 8/1987 | Cable |
| 4,687,582 | A | 8/1987 | Dixon |
| 4,750,494 | A | 6/1988 | King |
| 4,765,907 | A | 8/1988 | Scott |
| 4,826,663 | A | 5/1989 | Alberti |
| 4,828,693 | A | 5/1989 | Lindsay |
| 5,032,615 | A | 7/1991 | Ward et al. |
| 5,047,014 | A | 9/1991 | Mosebach et al. |
| 5,080,653 | A | 1/1992 | Voss |
| 5,092,886 | A | 3/1992 | Dobos-Hardy |
| 5,097,122 | A | 3/1992 | Coiman |
| 5,127,404 | A | 7/1992 | Wyborny |
| 5,192,132 | A | 3/1993 | Pelensky |
| 5,230,702 | A | 7/1993 | Lindsay |
| 5,284,470 | A | 2/1994 | Beltz |
| 5,302,288 | A | 4/1994 | Meidl |
| 5,305,745 | A | 4/1994 | Zacouto |
| 5,308,315 | A | 5/1994 | Khuri |
| 5,318,750 | A | 6/1994 | Lascombes |
| 5,399,157 | A | 3/1995 | Goux |
| 5,441,049 | A | 8/1995 | Masano |
| 5,442,969 | A | 8/1995 | Troutner |
| 5,445,610 | A | 8/1995 | Evert |
| 5,468,388 | A | 11/1995 | Goddard |
| 5,507,723 | A | 4/1996 | Keshaviah |
| 5,662,806 | A | 9/1997 | Keshaviah et al. |
| 5,683,432 | A | 11/1997 | Goedeke |
| 5,685,988 | A | 11/1997 | Malchesky |
| 5,716,400 | A | 2/1998 | Davidson |
| 5,744,031 | A | 4/1998 | Bene |
| 5,762,782 | A | 6/1998 | Kenley |
| 5,770,086 | A | 6/1998 | Indriksons |
| 5,849,179 | A | 12/1998 | Emerson |
| 5,858,186 | A | 1/1999 | Glass |
| 5,938,634 | A | 8/1999 | Hayden |
| 5,938,938 | A | 8/1999 | Bosetto |
| 5,944,684 | A | 8/1999 | Roberts et al. |
| 6,036,858 | A | 3/2000 | Carlsson |
| 6,048,732 | A | 4/2000 | Anslyn |
| 6,052,622 | A | 4/2000 | Holmstrom |
| 6,058,331 | A | 5/2000 | King |
| 6,114,176 | A | 9/2000 | Edgson et al. |
| 6,126,831 | A | 10/2000 | Goldau et al. |
| 6,171,480 | B1 | 1/2001 | Lee |
| 6,230,059 | B1 | 5/2001 | Duffin |
| 6,248,093 | B1 | 6/2001 | Moberg |
| 6,254,567 | B1 | 7/2001 | Treu |
| 6,321,101 | B1 | 11/2001 | Holmstrom |
| 6,362,591 | B1 | 3/2002 | Moberg |
| 6,363,279 | B1 | 3/2002 | Ben-Haim |
| 6,390,969 | B1 | 5/2002 | Bolling et al. |
| 6,491,993 | B1 | 12/2002 | Forbes |
| 6,521,184 | B1 | 2/2003 | Edgson et al. |
| 6,554,798 | B1 | 4/2003 | Mann |
| 6,555,986 | B2 | 4/2003 | Moberg |
| 6,565,525 | B1 | 5/2003 | Burbank et al. |
| 6,572,769 | B2 | 6/2003 | Rajan |
| 6,579,460 | B1 | 6/2003 | Willis |
| 6,585,675 | B1 | 7/2003 | O'Mahony et al. |
| 6,589,229 | B1 | 7/2003 | Connelly |
| 6,593,747 | B2 | 7/2003 | Puskas |
| 6,596,234 | B1 | 7/2003 | Schnell et al. |
| 6,602,399 | B1 | 8/2003 | Fromherz |
| 6,627,164 | B1 | 9/2003 | Wong |
| 6,666,840 | B1 | 12/2003 | Falkvall et al. |
| 6,676,608 | B1 | 1/2004 | Keren |
| 6,695,807 | B2 | 2/2004 | Bell et al. |
| 6,711,439 | B1 | 3/2004 | Bradley |
| 6,719,745 | B1 | 4/2004 | Taylor |
| 6,773,412 | B2 | 8/2004 | O'Mahony et al. |
| 6,814,724 | B2 | 11/2004 | Taylor |
| 6,818,196 | B2 | 11/2004 | Wong |
| 6,861,266 | B1 | 3/2005 | Sternby |
| 6,878,258 | B2 | 4/2005 | Hughes |
| 6,878,283 | B2 | 4/2005 | Thompson |
| 6,878,285 | B2 | 4/2005 | Hughes |
| 6,890,315 | B1 | 5/2005 | Levin |
| 6,923,782 | B2 | 8/2005 | O'Mahony et al. |
| 6,960,179 | B2 | 11/2005 | Gura |
| 7,029,456 | B2 | 4/2006 | Ware et al. |
| 7,033,498 | B2 | 4/2006 | Wong |
| 7,077,819 | B1 | 7/2006 | Goldau |
| 7,097,630 | B2 | 8/2006 | Gotch |
| 7,101,519 | B2 | 9/2006 | Wong |
| 7,128,750 | B1 | 10/2006 | Stergiopulos |
| 7,153,693 | B2 | 12/2006 | Tajiri |
| 7,208,092 | B2 | 4/2007 | Micheli |
| 7,241,272 | B2 | 7/2007 | Karoor et al. |
| 7,276,042 | B2 | 10/2007 | Polaschegg et al. |
| 7,309,323 | B2 | 12/2007 | Gura |
| 7,318,892 | B2 | 1/2008 | Connell |
| 7,326,576 | B2 | 2/2008 | Womble et al. |
| 7,384,543 | B2 | 6/2008 | Jonsson et al. |
| 7,435,342 | B2 | 10/2008 | Tsukamoto |
| 7,462,161 | B2 | 12/2008 | O'Mahony et al. |
| 7,488,447 | B2 | 2/2009 | Sternby |
| 7,537,688 | B2 | 5/2009 | Tarumi et al. |
| 7,544,300 | B2 | 6/2009 | Brugger et al. |
| 7,544,737 | B2 | 6/2009 | Poss et al. |
| 7,563,240 | B2 | 7/2009 | Gross et al. |
| 7,566,432 | B2 | 7/2009 | Wong |
| 7,575,564 | B2 | 8/2009 | Childers |
| 7,597,806 | B2 | 10/2009 | Uchi et al. |
| 7,674,231 | B2 | 3/2010 | McCombie |
| 7,674,237 | B2 | 3/2010 | O'Mahony et al. |
| 7,686,778 | B2 | 3/2010 | Burbank et al. |
| 7,704,361 | B2 | 4/2010 | Garde |
| 7,736,507 | B2 | 6/2010 | Wong |
| 7,754,852 | B2 | 7/2010 | Burnett |
| 7,756,572 | B1 | 7/2010 | Fard |
| 7,776,001 | B2 | 8/2010 | Brugger et al. |
| 7,776,006 | B2 | 8/2010 | Childers |
| 7,776,210 | B2 | 8/2010 | Rosenbaum et al. |
| 7,794,141 | B2 | 9/2010 | Perry |
| 7,794,419 | B2 | 9/2010 | Paolini |
| 7,850,635 | B2 | 12/2010 | Polaschegg et al. |
| 7,867,214 | B2 | 1/2011 | Childers |
| 7,901,376 | B2 | 3/2011 | Steck et al. |
| 7,905,853 | B2 | 3/2011 | Chapman et al. |
| 7,922,686 | B2 | 4/2011 | Childers |
| 7,922,911 | B2 | 4/2011 | Micheli |
| 7,947,179 | B2 | 5/2011 | Rosenbaum et al. |

(56) References Cited

U.S. PATENT DOCUMENTS

| | | |
|---|---|---|
| 7,955,289 B2 | 6/2011 | O'Mahony et al. |
| 7,955,290 B2 | 6/2011 | Karoor et al. |
| 7,967,022 B2 | 6/2011 | Grant |
| 7,981,082 B2 | 7/2011 | Wang |
| 7,988,854 B2 | 8/2011 | Tsukamoto |
| 8,002,726 B2 | 8/2011 | Karoor et al. |
| 8,012,118 B2 | 9/2011 | Curtin |
| 8,029,454 B2 | 10/2011 | Kelly et al. |
| 8,034,161 B2 | 10/2011 | Gura |
| 8,066,658 B2 | 11/2011 | Karoor et al. |
| 8,070,709 B2 | 12/2011 | Childers |
| 8,080,161 B2 | 12/2011 | Ding et al. |
| 8,087,303 B2 | 1/2012 | Beavis |
| 8,096,969 B2 | 1/2012 | Roberts et al. |
| 8,180,574 B2 | 5/2012 | Lo et al. |
| 8,182,673 B2 | 5/2012 | Childers et al. |
| 8,183,046 B2 | 5/2012 | Lu |
| 8,187,250 B2 | 5/2012 | Roberts et al. |
| 8,197,439 B2 | 6/2012 | Wang et al. |
| 8,206,591 B2 | 6/2012 | Kotanko et al. |
| 8,211,048 B2 | 7/2012 | Szamosfalvi et al. |
| 8,221,529 B2 | 7/2012 | Childers et al. |
| 8,226,595 B2 | 7/2012 | Childers et al. |
| 8,246,826 B2 | 8/2012 | Wilt |
| 8,267,881 B2 | 9/2012 | O'Mahony et al. |
| 8,273,049 B2 | 9/2012 | Demers |
| 8,292,594 B2 | 10/2012 | Tracey |
| 8,303,532 B2 | 11/2012 | Hamada et al. |
| 8,313,642 B2 | 11/2012 | Yu |
| 8,317,492 B2 | 11/2012 | Demers |
| 8,357,113 B2 | 1/2013 | Childers |
| 8,357,298 B2 | 1/2013 | Demers et al. |
| 8,366,316 B2 | 2/2013 | Kamen |
| 8,366,655 B2 | 2/2013 | Kamen |
| 8,376,999 B2 | 2/2013 | Busby et al. |
| 8,377,012 B2 | 2/2013 | Chapman et al. |
| 8,377,308 B2 | 2/2013 | Kreymann et al. |
| 8,388,567 B2 | 3/2013 | Rovatti |
| 8,404,491 B2 | 3/2013 | Li |
| 8,409,441 B2 | 4/2013 | Wilt |
| 8,409,444 B2 | 4/2013 | Wong |
| 8,449,487 B2 | 5/2013 | Spitalny |
| 8,480,607 B2 | 7/2013 | Davies |
| 8,499,780 B2 | 8/2013 | Wilt |
| 8,518,260 B2 | 8/2013 | Raimann |
| 8,535,525 B2 | 9/2013 | Heyes |
| 8,580,112 B2 | 11/2013 | Updyke |
| 8,597,227 B2 | 12/2013 | Childers |
| 8,647,506 B2 | 2/2014 | Wong |
| 8,696,626 B2 | 4/2014 | Kirsch |
| 8,733,559 B2 | 5/2014 | Wong |
| 8,764,981 B2 | 7/2014 | Ding |
| 8,777,892 B2 | 7/2014 | Sandford |
| 8,903,492 B2 | 12/2014 | Soykan |
| 9,144,640 B2 | 9/2015 | Pudil |
| 9,254,355 B2 | 2/2016 | Sandford |
| 9,527,015 B2 | 12/2016 | Chau |
| 10,297,593 B2 | 5/2019 | Gejo |
| 2001/0007931 A1 | 7/2001 | Blatter |
| 2001/0009756 A1 | 7/2001 | Hei et al. |
| 2002/0016550 A1 | 2/2002 | Sweeney |
| 2002/0027106 A1 | 3/2002 | Smith |
| 2002/0042561 A1 | 4/2002 | Schulman |
| 2002/0062098 A1 | 5/2002 | Cavicchioli et al. |
| 2002/0112609 A1* | 8/2002 | Wong .................. B01J 20/0277 96/131 |
| 2002/0117436 A1 | 8/2002 | Rajan |
| 2003/0080059 A1 | 5/2003 | Peterson |
| 2003/0097086 A1 | 5/2003 | Gura |
| 2003/0105435 A1 | 6/2003 | Taylor |
| 2003/0113931 A1 | 6/2003 | Pan |
| 2003/0114787 A1 | 6/2003 | Gura |
| 2003/0138348 A1 | 7/2003 | Bell et al. |
| 2003/0187479 A1 | 10/2003 | Thong |
| 2004/0019312 A1 | 1/2004 | Childers |
| 2004/0019320 A1 | 1/2004 | Childers |
| 2004/0030277 A1 | 2/2004 | O'Mahony et al. |
| 2004/0037986 A1 | 2/2004 | Yokochi et al. |
| 2004/0054315 A1 | 3/2004 | Levin et al. |
| 2004/0082903 A1 | 4/2004 | Micheli |
| 2004/0084358 A1 | 5/2004 | O'Mahony et al. |
| 2004/0099593 A1 | 5/2004 | DePaolis |
| 2004/0147900 A1 | 7/2004 | Polaschegg |
| 2004/0168963 A1 | 9/2004 | King |
| 2004/0215090 A1 | 10/2004 | Erkkila |
| 2004/0257409 A1 | 12/2004 | Cheok |
| 2005/0006296 A1 | 1/2005 | Sullivan |
| 2005/0056592 A1 | 3/2005 | Braunger et al. |
| 2005/0065760 A1 | 3/2005 | Murtfeldt |
| 2005/0101901 A1* | 5/2005 | Gura .................. A61M 1/3639 604/5.02 |
| 2005/0113796 A1 | 5/2005 | Taylor |
| 2005/0126961 A1 | 6/2005 | Bissler |
| 2005/0131332 A1 | 6/2005 | Kelly |
| 2005/0126998 A1 | 7/2005 | Childers |
| 2005/0148923 A1 | 7/2005 | Sternby |
| 2005/0150832 A1 | 7/2005 | Tsukamoto |
| 2005/0230313 A1 | 10/2005 | O'Mahony et al. |
| 2005/0234354 A1 | 10/2005 | Rowlandson |
| 2005/0234381 A1 | 10/2005 | Niemetz |
| 2005/0274658 A1 | 12/2005 | Rosenbaum |
| 2006/0025661 A1 | 2/2006 | Sweeney |
| 2006/0037483 A1 | 2/2006 | Kief |
| 2006/0217771 A1 | 2/2006 | Soykan |
| 2006/0157413 A1 | 7/2006 | Bene |
| 2006/0189926 A1 | 8/2006 | Hall et al. |
| 2006/0195064 A1 | 8/2006 | Plahey |
| 2006/0226079 A1 | 10/2006 | Mori |
| 2006/0241543 A1 | 10/2006 | Gura |
| 2006/0241709 A1 | 10/2006 | Soykan |
| 2006/0264894 A1 | 11/2006 | Moberg |
| 2007/0007208 A1 | 1/2007 | Brugger |
| 2007/0055296 A1 | 3/2007 | Stergiopulos |
| 2007/0066928 A1 | 3/2007 | Lannoy |
| 2007/0138011 A1 | 6/2007 | Hofmann |
| 2007/0175827 A1 | 8/2007 | Wariar |
| 2007/0179431 A1 | 8/2007 | Roberts |
| 2007/0213665 A1 | 9/2007 | Curtin |
| 2007/0215545 A1 | 9/2007 | Bissler |
| 2007/0243113 A1 | 10/2007 | DiLeo |
| 2007/0255250 A1 | 11/2007 | Moberg |
| 2008/0006570 A1 | 1/2008 | Gura |
| 2008/0011664 A1 | 1/2008 | Karoor et al. |
| 2008/0015493 A1 | 1/2008 | Childers et al. |
| 2008/0021337 A1 | 1/2008 | Li |
| 2008/0051696 A1 | 2/2008 | Curtin |
| 2008/0053905 A9 | 3/2008 | Brugger |
| 2008/0067132 A1 | 3/2008 | Ross |
| 2008/0215247 A1 | 9/2008 | Tonelli |
| 2008/0217245 A1 | 9/2008 | Rambod |
| 2008/0241031 A1 | 10/2008 | Li |
| 2008/0292935 A1 | 11/2008 | Roelofs |
| 2009/0020471 A1 | 1/2009 | Tsukamoto |
| 2009/0078636 A1 | 3/2009 | Uchi |
| 2009/0084199 A1 | 4/2009 | Wright |
| 2009/0101552 A1 | 4/2009 | Fulkerson |
| 2009/0101577 A1 | 4/2009 | Fulkerson |
| 2009/0120864 A1 | 5/2009 | Fulkerson |
| 2009/0127193 A1 | 5/2009 | Updyke |
| 2009/0149795 A1 | 6/2009 | O'Mahony et al. |
| 2009/0216045 A1 | 8/2009 | Singh |
| 2009/0266358 A1 | 10/2009 | Sacristan Rock |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2010/0004588 A1 | 1/2010 | Yeh et al. |
| 2010/0007838 A1 | 1/2010 | Fujimoto |
| 2010/0010429 A1 | 1/2010 | Childers |
| 2010/0018923 A1 | 1/2010 | Rohde et al. |
| 2010/0030151 A1 | 2/2010 | Kirsch |
| 2010/0051529 A1 | 3/2010 | Grant et al. |
| 2010/0051552 A1 | 3/2010 | Rohde |
| 2010/0076364 A1 | 3/2010 | O'Mahony et al. |

(56) References Cited

U.S. PATENT DOCUMENTS

| | | |
|---|---|---|
| 2010/0078381 A1 | 4/2010 | Merchant |
| 2010/0078387 A1 | 4/2010 | Wong |
| 2010/0084330 A1 | 4/2010 | Wong |
| 2010/0094158 A1 | 4/2010 | Solem |
| 2010/0100027 A1* | 4/2010 | Schilthuizen ....... A61M 1/3486 604/6.09 |
| 2010/0101195 A1* | 4/2010 | Clements ............ B01D 46/521 55/341.5 |
| 2010/0102190 A1 | 4/2010 | Zhu et al. |
| 2010/0114001 A1 | 5/2010 | O'Mahony |
| 2010/0114012 A1 | 5/2010 | Sandford et al. |
| 2010/0137693 A1 | 6/2010 | Porras |
| 2010/0168546 A1 | 7/2010 | Kamath |
| 2010/0168641 A1 | 7/2010 | O'Mahony et al. |
| 2010/0213127 A1 | 8/2010 | Castellarnau |
| 2010/0217181 A1 | 8/2010 | Roberts et al. |
| 2010/0224492 A1 | 9/2010 | Ding et al. |
| 2010/0234795 A1 | 9/2010 | Wallenas |
| 2010/0241045 A1 | 9/2010 | Kelly |
| 2010/0252490 A1 | 10/2010 | Fulkerson |
| 2010/0312172 A1 | 12/2010 | Hoffman |
| 2010/0312174 A1 | 12/2010 | Hoffman |
| 2010/0314314 A1 | 12/2010 | Ding |
| 2010/0326911 A1 | 12/2010 | Rosenbaum |
| 2011/0009798 A1 | 1/2011 | Kelly |
| 2011/0017665 A1 | 1/2011 | Updyke |
| 2011/0048949 A1 | 3/2011 | Ding |
| 2011/0066043 A1 | 3/2011 | Banet |
| 2011/0077574 A1 | 3/2011 | Sigg |
| 2011/0079558 A1 | 4/2011 | Raimann |
| 2011/0087187 A1 | 4/2011 | Beck |
| 2011/0130666 A1 | 6/2011 | Dong |
| 2011/0163034 A1 | 7/2011 | Castellarnau |
| 2011/0171713 A1 | 7/2011 | Bluchel et al. |
| 2011/0184340 A1 | 7/2011 | Tan |
| 2011/0220562 A1 | 9/2011 | Beiriger |
| 2011/0247973 A1 | 10/2011 | Sargand |
| 2011/0272337 A1 | 11/2011 | Palmer |
| 2011/0272352 A1 | 11/2011 | Braig |
| 2011/0297593 A1 | 12/2011 | Kelly et al. |
| 2011/0315611 A1 | 12/2011 | Fulkerson |
| 2011/0315632 A1 | 12/2011 | Freije |
| 2012/0016228 A1 | 1/2012 | Kroh |
| 2012/0018377 A1 | 1/2012 | Tsukamoto |
| 2012/0083729 A1 | 4/2012 | Childers |
| 2012/0085707 A1 | 4/2012 | Beiriger |
| 2012/0092025 A1 | 4/2012 | Volker |
| 2012/0095402 A1 | 4/2012 | Lande |
| 2012/0115248 A1 | 5/2012 | Ansyln |
| 2012/0220528 A1 | 8/2012 | Vanantwerp |
| 2012/0248017 A1* | 10/2012 | Beiriger ............... A61M 1/1605 210/143 |
| 2012/0258545 A1 | 10/2012 | Ash |
| 2012/0258546 A1 | 10/2012 | Marran |
| 2012/0273354 A1 | 11/2012 | Orhan et al. |
| 2012/0273415 A1 | 11/2012 | Gerber |
| 2012/0273420 A1 | 11/2012 | Gerber |
| 2012/0277546 A1 | 11/2012 | Soykan |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0303079 A1 | 11/2012 | Mahajan |
| 2013/0006128 A1 | 1/2013 | Olde et al. |
| 2013/0018095 A1 | 1/2013 | Vath |
| 2013/0019179 A1 | 1/2013 | Zhao |
| 2013/0020237 A1 | 1/2013 | Wilt et al. |
| 2013/0023812 A1 | 1/2013 | Hasegawa et al. |
| 2013/0025357 A1 | 1/2013 | Noack et al. |
| 2013/0027214 A1 | 1/2013 | Eng |
| 2013/0028809 A1 | 1/2013 | Barton |
| 2013/0030347 A1 | 1/2013 | Sugioka |
| 2013/0030348 A1 | 1/2013 | Lauer |
| 2013/0030356 A1 | 1/2013 | Ding |
| 2013/0037142 A1 | 2/2013 | Farrell |
| 2013/0037465 A1 | 2/2013 | Heyes |
| 2013/0056418 A1 | 3/2013 | Kopperschmidt et al. |
| 2013/0072895 A1 | 3/2013 | Kreischer et al. |
| 2013/0075314 A1 | 3/2013 | Nikolic |
| 2013/0087210 A1 | 4/2013 | Brandl et al. |
| 2013/0110028 A1 | 5/2013 | Bachmann et al. |
| 2013/0116578 A1 | 5/2013 | An |
| 2013/0199998 A1 | 8/2013 | Kelly |
| 2013/0213890 A1 | 8/2013 | Kelly |
| 2013/0213891 A1 | 8/2013 | Karoor |
| 2013/0228516 A1 | 9/2013 | Jonsson |
| 2013/0274642 A1 | 10/2013 | Soykan |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0001112 A1 | 1/2014 | Karoor |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0138294 A1 | 5/2014 | Fulkerson |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0190885 A1 | 7/2014 | Meyer |
| 2014/0190886 A1 | 7/2014 | Pudil |
| 2014/0190891 A1 | 7/2014 | Lura |
| 2014/0217028 A1 | 8/2014 | Pudil |
| 2014/0217030 A1 | 8/2014 | Meyer |
| 2014/0220699 A1 | 8/2014 | Pudil |
| 2014/0251908 A1 | 9/2014 | Ding |
| 2014/0326671 A1 | 11/2014 | Kelly |
| 2014/0336568 A1 | 11/2014 | Wong |
| 2015/0057602 A1 | 2/2015 | Mason |
| 2015/0108069 A1 | 4/2015 | Merchant |
| 2015/0108609 A1 | 4/2015 | Kushida |
| 2015/0114891 A1 | 4/2015 | Meyer |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0251161 A1 | 9/2015 | Pudil |
| 2015/0251162 A1 | 9/2015 | Pudil |
| 2015/0258266 A1 | 9/2015 | Merchant |
| 2015/0306292 A1 | 10/2015 | Pudil |
| 2015/0367051 A1 | 12/2015 | Gerber |
| 2015/0367052 A1 | 12/2015 | Gerber |
| 2015/0367055 A1 | 12/2015 | Pudil |
| 2015/0367056 A1 | 12/2015 | Gerber |
| 2015/0367057 A1 | 12/2015 | Gerber |
| 2015/0367058 A1 | 12/2015 | Gerber |
| 2015/0367059 A1 | 12/2015 | Gerber |
| 2015/0367060 A1 | 12/2015 | Gerber |
| 2016/0236188 A1 | 8/2016 | Menon |
| 2016/0243540 A1 | 8/2016 | Menon |
| 2016/0243541 A1 | 8/2016 | Menon |
| 2017/0246367 A9* | 8/2017 | Pudil ..................... B01J 20/06 |

FOREIGN PATENT DOCUMENTS

| | | |
|---|---|---|
| CN | 103402563 A | 11/2013 |
| CN | 104936633 | 9/2015 |
| CN | 105658326 A | 6/2016 |
| DE | 3110128 A1 | 9/1982 |
| DE | 102011052188 | 1/2013 |
| EP | 266795 A2 | 11/1987 |
| EP | 0264695 | 4/1988 |
| EP | 0614081 A1 | 10/1993 |
| EP | 0614081 B1 | 7/2000 |
| EP | 711182 B1 | 6/2003 |
| EP | 1364666 A1 | 11/2003 |
| EP | 0906768 B1 | 2/2004 |
| EP | 1701752 A2 | 9/2006 |
| EP | 1450879 | 10/2008 |

(56) References Cited

FOREIGN PATENT DOCUMENTS

| | | |
|---|---|---|
| EP | 1991289 | 11/2008 |
| EP | 1592494 B1 | 6/2009 |
| EP | 2100553 A1 | 9/2009 |
| EP | 2575827 A2 | 12/2010 |
| EP | 2576453 A2 | 12/2011 |
| EP | 2446908 | 5/2012 |
| EP | 2701580 | 11/2012 |
| EP | 2701595 | 11/2012 |
| EP | 1545652 B1 | 1/2013 |
| EP | 1684625 B1 | 1/2013 |
| EP | 2142234 B1 | 1/2013 |
| EP | 2550984 A1 | 1/2013 |
| EP | 1345856 B1 | 3/2013 |
| EP | 1938849 B1 | 3/2013 |
| EP | 2219703 B1 | 3/2013 |
| EP | 2564884 A1 | 3/2013 |
| EP | 2564885 A1 | 3/2013 |
| EP | 2344220 B1 | 4/2013 |
| EP | 1345687 | 6/2013 |
| EP | 2701596 | 3/2014 |
| JP | S5070281 A | 6/1975 |
| JP | S51-55193 | 5/1976 |
| JP | S51-131393 | 11/1976 |
| JP | S61164562 | 7/1986 |
| JP | 2981573 | 11/1999 |
| JP | 2005511250 | 4/2005 |
| JP | H4-90963 | 5/2005 |
| JP | 2007-44602 A | 2/2007 |
| JP | 200744602 | 2/2007 |
| JP | 200744602 A | 2/2007 |
| JP | 5099464 | 10/2012 |
| JP | 2013502987 | 10/2013 |
| NL | 197301897 A * | 8/1973 |
| WO | 9106326 A1 | 5/1991 |
| WO | 9532010 A1 | 11/1995 |
| WO | 9937342 | 7/1999 |
| WO | 2000038591 A2 | 7/2000 |
| WO | 0057935 | 10/2000 |
| WO | 200066197 A1 | 11/2000 |
| WO | 200170307 A1 | 9/2001 |
| WO | 2001085295 A2 | 9/2001 |
| WO | 0185295 A2 | 11/2001 |
| WO | 2002043859 | 6/2002 |
| WO | 2003043677 A2 | 5/2003 |
| WO | 2003043680 | 5/2003 |
| WO | WO 2003041764 | 5/2003 |
| WO | 2003051422 A2 | 6/2003 |
| WO | 2004008826 | 1/2004 |
| WO | 2004009156 | 1/2004 |
| WO | 2004030716 A2 | 4/2004 |
| WO | 2004030717 A2 | 4/2004 |
| WO | 2004064616 A2 | 8/2004 |
| WO | 2004062710 A3 | 10/2004 |
| WO | WO 2005/062973 A3 | 7/2005 |
| WO | 2005123230 | 12/2005 |
| WO | 2005123230 A2 | 12/2005 |
| WO | 2007089855 A2 | 8/2007 |
| WO | WO 20070103411 | 9/2007 |
| WO | 2008075951 A1 | 6/2008 |
| WO | 2009026603 A1 | 3/2009 |
| WO | 2009064984 | 5/2009 |
| WO | 2009157877 A1 | 12/2009 |
| WO | 2009157878 A1 | 12/2009 |
| WO | 20090157877 | 12/2009 |
| WO | 2010028860 A1 | 3/2010 |
| WO | 2010102190 A4 | 11/2010 |
| WO | 2010141949 | 12/2010 |
| WO | WO 2011/017215 | 2/2011 |
| WO | 2011025705 A1 | 3/2011 |
| WO | WO2014121238 A1 | 4/2011 |
| WO | 2012148781 | 11/2012 |
| WO | 2012148786 | 11/2012 |
| WO | 2012148789 | 11/2012 |
| WO | 2012162515 A2 | 11/2012 |
| WO | 20120277551 | 11/2012 |
| WO | 2012172398 | 12/2012 |
| WO | 2013019179 | 2/2013 |
| WO | 2013019179 A1 | 2/2013 |
| WO | 2013019994 A2 | 2/2013 |
| WO | 2013022024 A1 | 2/2013 |
| WO | 2013022837 A1 | 2/2013 |
| WO | 2013025957 | 2/2013 |
| WO | 2013027214 | 2/2013 |
| WO | 2013028809 A3 | 2/2013 |
| WO | WO 2013/019179 | 2/2013 |
| WO | WO 2013/019994 | 2/2013 |
| WO | WO 2013-025957 | 2/2013 |
| WO | WO 2013-028809 | 2/2013 |
| WO | WO 2013/028809 | 2/2013 |
| WO | WO 2013019179 | 2/2013 |
| WO | 2013030642 A1 | 3/2013 |
| WO | 2013030643 A1 | 3/2013 |
| WO | 2012060700 | 5/2013 |
| WO | 2013025844 A3 | 5/2013 |
| WO | 2013101888 | 7/2013 |
| WO | 2013103607 A1 | 7/2013 |
| WO | 2013103906 | 7/2013 |
| WO | WO 2013/103607 | 7/2013 |
| WO | WO 2013109922 | 7/2013 |
| WO | 2013114063 A1 | 8/2013 |
| WO | 2013121162 A1 | 8/2013 |
| WO | 14066254 | 5/2014 |
| WO | 14066255 | 5/2014 |
| WO | 14077082 | 5/2014 |
| WO | 2014121162 | 8/2014 |
| WO | 2014121163 | 8/2014 |
| WO | 2014121167 | 8/2014 |
| WO | 2014121169 | 8/2014 |
| WO | 2015060914 | 4/2015 |
| WO | WO 2015/080895 | 4/2015 |
| WO | WO 2015060914 | 4/2015 |
| WO | WO 2015/126879 | 8/2015 |
| WO | 2015142624 | 9/2015 |
| WO | 2015199764 | 12/2015 |
| WO | 2015199765 | 12/2015 |
| WO | 2015199863 | 12/2015 |
| WO | 2015199864 | 12/2015 |
| WO | WO 2015-199863 | 12/2015 |
| WO | WO 2015-199864 | 12/2015 |
| WO | WO 2015199765 | 12/2015 |
| WO | WO 2016/191039 | 12/2016 |

OTHER PUBLICATIONS

U.S. Appl. No. 13/565,733, filed Aug. 2, 2012, Medtronic.
U.S. Appl. No. 13/757,693, filed Feb. 1, 2013, Medtronic.
U.S. Appl. No. 13/757,709, filed Feb. 1, 2013, Medtronic.
U.S. Appl. No. 13/757,728, filed Feb. 1, 2013, Medtronic.
U.S. Appl. No. 13/836,538, filed Mar. 15, 2013, Medtronic.
U.S. Appl. No. 61/760,033, filed Feb. 1, 2013, Medtronic.
U.S. Appl. No. 14/637,606_OA.
U.S. Appl. No. 14/645,394_OA.
[NPL105] Brynda, et. al., The detection of toman 2-microglcbuiin by grating coupler immunosensor with three dimensional antibody networks. Biosensors & Bioelectronics, 1999, 363-368, 14(4).
[NPL10] Wheaton, et al., Dowex Ion Exchange Resins—Fundamentals of Ion Exchange; Jun. 2000, pp. 1-9. http://www.dow.com/scripts/litorder.asp?filepath=liquidseps/pdfs/noreg/177-01837.pdf.
[NPL111] Zhong, et. al., Miniature urea sensor based on H(+)-ion sensitive field effect transistor and its application in clinical analysis, Chin. J. Biotechnol., 1992, 57-65. 8(1).
[NPL119] PCT/US2012/034331, International Search Report and Written Opinion dated Jul. 9, 2012.
[NPL121] Roberts M, The regenerative dialysis (REDY) sorbent system. Nephrology, 1998, 275-278:4.
[NPL138] U.S. Appl. No. 61/480,544.
[NPL139] U.S. Appl. No. 61/480,541 dated Apr. 29, 2011.
[NPL142] Hemametrics, Crit-Line Hematocrit Accuracy, 2003, 1-5, vol. 1, Tech Note No. 11 (Rev. D).

(56) References Cited

OTHER PUBLICATIONS

[NPL144] Weissman, S., et al., Hydroxyurea-induced hepatitis in human immunodeficiency virus-positive patients. Clin. Infec. Dis, (Jul. 29, 1999): 223-224.
[NPL146] PCT/US2012/034334, International Search Report, dated Jul. 6, 2012.
[NPL147] PCT/US2012/034335, International Search Report, dated Sep. 5, 2012.
[NPL148] PCT/US/2012/034327, International Search Report, dated Aug. 13, 2013.
[NPL149] PCT/US/2012/034329, International Search Report, dated Dec. 3, 2012.
[NPL162] International Search Report from PCT/US2012/051946 dated Mar. 4, 2013.
[NPL163] U.S. Appl. No. 61/526,209.
[NPL169] Wang, Fundamentals of intrathoracic impedance monitoring in heart failure, Am. J. Cardiology, 2007, 3G-10G: Suppl.
[NPL16] PCT/US2014/067650 International Search Report Written Opinion dated Mar. 9, 2015.
[NPL176] Bleyer, et. al., Sudden and cardiac death rated in hemodialysis patients, Kidney International. 1999, 1553-1559: 55.
[NPL187] PCT/US2012/034333, International Preliminary Report on Patentability, dated Oct. 29, 2013.
[NPL188] PCT/US2012/034333, International Search Report, dated Aug. 29, 2012.
[NPL188] PCT/US2012/034333, International Search Report, dated Aug. 29, 2013.
[NPL197] PCT/US2012/034330, International Preliminary Report on Patentability, dated Oct. 29, 2013.
[NPL1] PCT/US2014/065950 International Search Report and Written Opinion dated Feb. 24, 2015.
[NPL205] Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
[NPL217] U.S. Appl. No. 13/757,722, filed Feb. 1, 2013.
[NPL218] U.S. Appl. No. 13/757,794, filed Feb. 2, 2012.
[NPL219] U.S. Appl. No. 13/791,755, filed Mar. 8, 2013.
[NPL21] U.S. Appl. No. 13/424,479 dated Nov. 1, 2012.
[NPL220] U.S. Appl. No. 13/757,792, filed Feb. 2, 2013.
[NPL222] U.S. Appl. No. 13/757,794, filed Feb. 2, 2013.
[NPL227] U.S. Appl. No. 13/837,287, filed Mar. 15, 2013.
[NPL22] U.S. Appl. No. 13/424,429 dated Nov. 1, 2012.
[NPL230] Redfield, et. al, Restoration of renal response to atria! natriuretic factor in experimental low-output heat failure, Am. J. Physiol., Oct. 1, 1989, R917-923:257.
[NPL231] Rogoza, et. al., Validation of A&D UA-767 device for the self-measurement of blood pressure, Blood Pressure Monitoring, 2000, 227-231, 5(4).
[NPL234] Lima, et. al., An electrochemical sensor based on nanostructure hollsndite-type manganese oxide for detection of potassium ion, Sensors, Aug. 24, 2009, 6613-8625, 9.
[NPL235] MaClean, et, al., Effects of hindlimb contraction on pressor and muscle interstitial metabolite responses in the cat, J. App. Physiol., 1998, 1583-1592, 85(4).
[NPL237] U.S. Appl. No. 13/757,693, dated Feb. 1, 2013.
[NPL238] PCT Application, PCT/US20013/020404, filed Jan. 4, 2013.
[NPL23] U.S. Appl. No. 13/424,525.
[NPL240] U.S. Appl. No. 13/836,973, filed Mar. 15, 2013.
[NPL241] U.S. Appl. No. 14/259,655, filed Apr. 23, 2014.
[NPL242] U.S. Appl. No. 14/259,589, filed Apr. 23, 2014.
[NPL243] U.S. Appl. No. 13/757,693, filed Jan. 4, 2013.
[NPL244] U.S. Appl. No. 13/836,079, filed Mar. 15, 2013.
[NPL245] U.S. Appl. No. 14/240,129, filed Aug. 22, 2013.
[NPL246] PCT/US2014/014346 International Search Report and Written Opinion.
[NPL247] U.S. Appl. No. 13/835,735, filed Mar. 15, 2013.
[NPL248] PCT/US2014/014345 International Search Report and Written Opinion, dated May 2014.
[NPL250] U.S. Appl. No. 13/835,735 IDS, filed Jun. 13, 2013.
[NPL264] PCT/US2014/014357 International Search Report and Written Opinion dated May 19, 2014.
[NPL268] Ronco et al. 2008, Cardiorenal Syndrome, Journal American College Cardiology, 52:1527-1539, Abstract.
[NPL26] Overgaard, et. al., Activity-induced recovery of excitability in K+-depressed rat soleus muscle, Am. J. p. 280: R48-R55, Jan 1, 2001.
[NPL27] Overgaard. et. al., Relations between excitability and contractility in rate soleusmuscle: role of the NA+-K+ pump and NA+-K-S gradients. Journal of Physiology, 1999, 215-225, 518(1).
[NPL2] PCT/US2015/032492 International Search Report dated Nov. 19, 2015.
[NPL306] Coast, et al. 1990, An approach to Cardiac Arrhythmia analysis Using Hidden Markov Models, IEEE Transactions on Biomedical Engineering. 1990, 37(9):826-835.
[NPL310] U.S. Appl. No. 61/480,532.
[NPL317] U.S. Appl. No. 61/480,530.
[NPL318] U.S. Appl. No. 61/480,528 dated Apr. 29, 2011.
[NPL32] Secemsky, et. al, High prevalence of cardiac autonomic dysfunction and T-wave alternans in dialysis patients. Heart Rhythm, Apr. 2011, 592-598 : vol. 8, No. 4.
[NPL35] Wei, et. al., Fullerene-cryptand coated piezoelectric crystal urea sensor based on urease, Analytica Chimica Acta, 2001,77-85:437.
[NPL376] Gambro AK 96 Dialysis Machine Operators Manual, Dec. 2012. p. 1-140.
[NPL376] Gambro AK 96 Dialysis Machine Operators Manual, Dec. 2012. p. 141-280.
[NPL376] Gambro AK 96 Dialysis Machine Operators Manual, Dec. 2012. p. 281-420.
[NPL376] Gambro AK 96 Dialysis Machine Operators Manual, Dec. 2012. p. 421-534.
[NPL37] U.S. Appl. No. 13/368,225 dated Feb. 7, 2012.
[NPL383] Leifer et al., A Study on the Temperature Variation of Rise Velocity for Large Clean Bubbles, J. Atmospheric & Oceanic Tech., vol. 17, pp. 1392-1402, Oct. 2000.
[NPL384] Talaia, Terminal Velocity of a Bubble Rise in a Liquid Column, World Acad. of Sci., Engineering & Tech., vol. 28, pp. 264-68, Published Jan. 1, 2007.
[NPL386] The FHN Trial Group. In-Center. Hemodialysis Six Times per Week versus Three Times per Week, New England Journal of Medicine, 2010 Abstract.
[NPL387] Gotch FA, Sargent JA A mechanistic analysis of the National Cooperative Dialysis Study (NCDS). Kidney int. 1985: 28:526-34.
[NPL388] Daugirdas JT. Second generation logarithmic estimates of single-pool variable volume Kt/V and analysis of error. J Am Soc Nephrol, 1993: 4:1205-13.
[NPL389] Steil et al. Intl Journ Artif Organs, 1993, In Vivo Verification of an Automatic Noninvasive System for Real Time Kt Evaluation, ASAIO J., 1993, 39:M348-52.
[NPL39] PCT/US2012/034332, International Search Report, dated Jul. 5, 2012.
[NPL3] PCT/US2015/019901 International Search Report and Written Opinion dated Jun. 5, 2015.
[NPL46] Siegenthaler, et al., Pulmonary fluid status monitoring with intrathoracic impedance, Journal of Clinical Monitoring and Computing, 24:449-451, published Jan. 12, 2011.
[NPL47] U.S. Appl. No. 61/480,544.
[NPL494] John Wm Agar: Review: Understanding sorbent dialysis systems, Nephrology, vol. 15, No. 4, Jun. 1, 2010, pp. 406-411.
[NPL499] EP. App. 14746193.3 Search Report dated Oct. 19, 2016.
[NPL4] PCT/US2015/016270 International Search Report and Written Opinion dated Jun. 5, 2015.
[NPL518] Office Action in U.S. Appl. No. 14/269,589, dated Nov. 4, 2016.
[NPL519] Office Action in U.S. Appl. No. 13/586,824 dated Dec. 21, 2015.
[NPL520] Office Action in U.S. Appl. No. 13/586,824 dated Jun. 4, 2015.
[NPL532] Eureopean Search Report for App. No. EP14745643 dated Oct. 6, 2016.

(56) References Cited

OTHER PUBLICATIONS

[NPL534] Office Action in U.S. Appl. No. 13/586,824 dated Dec. 21, 2015.
[NPL548] PCT/US15/18587 International Preliminary Report on Patentability dated Jun. 6, 2016.
[NPL550] European Search Opinion for App. No. EP12826180 dated Mar. 19, 2015.
[NPL551] European Search Opinion for App. No. EP12826180 dated Jan. 18, 2016.
[NPL552] Khanna, Ramesh, R.T. Krediet, and Karl D. Nolph. Nolph and Gokals Textbook of Peritoneal Dialysis New York: Springer 2009. Print.
[NPL553] Ruperez et al., Comparison of a tubular pulsatile pump and a volumetric pump for continuous venovenous renal replacement therapy in a pediatric animal model, 51 ASAIO J. 372, 372-375 (2005).
[NPL554] St. Peter et al., Liver and kidney preservation by perfusion, 359 The Lancet 604, 606(2002).
[NPL555] Dasselaar et al., Measurement of relative blood volume changes during hemodialysis: merits and limitations, 20 Nephrol Dial Transpl. 2043, 2043-2044 (2005).
[NPL556] Ralph T. Yang, Adsorbents: Fundamentals and Applications 109 (2003).
[NPL557] Henny H. Billett, Hemoglobin and Hematocrit, in Clinical Methods: The History, Physical, and Laboratory Examinations 719(HK Walker, WD Hall, & JW Hurst ed., 1990).
[NPL558] Office Action in U.S. Appl. No. 13/565,733 dated Jan. 11, 2016.
[NPL559] Office Action in U.S. Appl. No. 13/565,733 dated Jun. 11, 2015.
[NPL55] U.S. Appl. No. 13/424,454.
[NPL560] Office Action in U.S. Appl. No. 13/586,824 dated Jun. 4, 2015.
[NPL561] Office Action in U.S. Appl. No. 13/757,792 dated Jun. 2, 2016.
[NPL562] Office Action in U.S. Appl. No. 13/757,796 dated Apr. 13, 2015.
[NPL563] Office Action in U.S. Appl. No. 13/757,796 dated Dec. 21, 2015.
[NPL564] Office Action in U.S. Appl. No. 13/835,735 dated Oct. 13, 2015.
[NPL565] Office Action in U.S. Appl. No. 13/836,079 dated Apr. 17, 2015.
[NPL566] Office Action in U.S. Appl. No. 13/836,079 dated Jun. 30, 2016.
[NPL569] Office Action in U.S. Appl. No. 13/791,755 dated Mar. 16, 2016.
[NPL570] Office Action in U.S. Appl. No. 13/791,755 dated Aug. 9, 2016.
[NPL571] Office Action in U.S. Appl. No. 13/835,735 dated Jun. 16, 2016.
[NPL572] Office Action in U.S. Appl. No. 13/836,079 dated Nov. 6, 2015.
[NPL57] U.S. Appl. No. 13/424,467.
[NPL584] Office Action in App. No. AU 2015280604 dated Apr. 8, 2016.
[NPL586] International Search Report from International Application No. PCT/US2014/014347 dated May 9, 2014.
[NPL590] PCT/US2016/030319 Written Opinion dated Jul. 27, 2016.
[NPL591] PCT/US2016/030320 Written Opinion dated Jul. 27, 2016.
[NPL596] PCT/US2012/014347, International Search Report.
[NPL5] PCT/US2015/016273 International Search Report and Written Opinion dated Jun. 9, 2015.
[NPL601] Wester et al., A regenerable postassium and phosphate sorbent system to enhance dialysis efficacy and device portability: an in vitro study Nephrol Dial Transplant (2013) 28: 2364-2371 Jul. 3, 2013.

[NPL602] Office Action in App. No. JP 2016-515476 dated Dec. 26, 2016.
[NPL603] Japanese Patent Publication No. S50-70281A.
[NPL605] PCT/US2015/032494 Written Opinion dated Nov. 19, 2015.
[NPL606] PCT/US2015/032494 International Search Report dated Nov. 19, 2015.
[NPL607] PCT/US2015/019901 International Preliminary Report on Patentability dated May 27, 2016.
[NPL608] PCT/US2015/019901 Written Opinion dated May 27, 2016.
[NPL609] PCT/US2015/019901 Written Opinion dated Jun. 5, 2015.
[NPL610] PCT/US2015/019901 International Search Report dated Jun. 5, 2015.
[NPL611] PCT/US2015/032485 International Preliminary Report on Patentability dated May 11, 2016.
[NPL612] PCT/US2015/032485 International Preliminary Report on Patentability dated May 11, 2016.
[NPL613] PCT/US20115/032485 International Preliminary Report on Patentability dated May 11, 2016.
[NPL614] PCT/US2016/030304 International Search Report dated Jul. 27, 2016.
[NPL615] PCT/US2016/030304 Written Opinion dated Jul. 27, 2016.
[NPL616] PCT/US2016/030312 Written Opinion dated Jul. 28, 2016.
[NPL617] PCT/US2016/030312 International Search Report dated Jul. 28, 2016.
[NPL618] PCT/US2016/030319 International Search Report dated Jul. 27, 2016.
[NPL619] PCT/US2016/030319 Written Opinion dated Jul. 27, 2016.
[NPL620] PCT/US2016/030320 Written Opinion dated Jul. 28, 2016.
[NPL621] PCT/US2016/030320 International Search Report dated Jul. 28, 2016.
[NPL622] PCT/US2015/032485 Written Opinion dated Oct. 16, 2015.
[NPL623] PCT/US2015/032485 Written Opinion dated Oct. 16, 2016.
[NPL626] PCT/US2015/032485 International Search Report and Written Opinion dated Oct. 16, 2015.
[NPL62] U.S. Appl. No. 13/424,533.
[NPL634] PCT/US2016/030320 International Preliminary Report on Patentability, dated Apr. 20, 2017.
[NPL654] International Preliminary Report from International Application No. PCT/US2014/014348 dated Jan. 9, 2015.
[NPL655] European Search Report from European Application No. EP 14746193.3 dated Oct. 19, 2016.
[NPL656] European Search Report from European Application No. EP 14746193.3 dated Jun. 8, 2016.
[NPL657] PCT/US2014/014345 Written Opinion dated Jun. 24, 2015.
[NPL658] PCT/US2014/014345 International Search Report and Written Opinion dated May 30, 2014.
[NPL659] Office Action in European Application No. 14746428.03 dated Feb. 8, 2017.
[NPL660] European Search Report in European Application No. 14746428.03 dated Aug. 25, 2016.
[NPL661] PCT/US2014/014346 Writtent Opinion dated Apr. 10, 2015.
[NPL662] PCT/US2014/014346 International Search Report and Writtent Opinion dated May 23, 2014.
[NPL663] EP 14746415.0 European Search Report dated Aug. 22, 2016.
[NPL664] Office Action in European Application No. EP 14746415.0 dated Apr. 19, 2017.
[NPL670] Office Action in European Application No. 14746415.0 dated Apr. 19, 2017.
[NPL67] U.S. Appl. No. 13/424,490.
[NPL681] PCT/US2015/020047 International Search Report and Written Opinion dated Jun. 29, 2015.

(56) References Cited

OTHER PUBLICATIONS

[NPL682] PCT/US2015/020047 International Preliminary Report on Patentability dated Jun. 30, 2015.
[NPL684] PCT/US2015/020044 Written Opinion dated Jun. 21, 2016.
[NPL685] PCT/US2015/020044 International Preliminary Report on Patentability dated Nov. 4, 2016.
[NPL686] PCT/US2015/020044 International Search Report dated Jun. 30, 2015.
[NPL688] US2015/019881 Written Opinion dated Jun. 16, 2016.
[NPL689] US2015/019881 Written Opinion dated May 9, 2016.
[NPL68] U.S. Appl. No. 13/424,517.
[NPL690] US2015/019881 International Search Report and Written Opinion dated Jun. 29, 2015.
[NPL692] PCT/US2014/065950 International Preliminary Report on Patentability dated Oct. 28, 2015.
[NPL696] PCT/US2015/032485 Written Opinion dated May 9, 2016.
[NPL6] PCT/US2015/032492 Written Opinion dated Nov. 19, 2015.
[NPL720] PCT/US2015/019901 International Search Report and Written Opinion dated Jun. 5, 2015.
[NPL721] PCT/US2015/019901 International Preliminary Report on Patentability dated May 27, 2016.
[NPL722] PCT/US2015/032494 International Preliminary Report on Patentablity dated Dec. 27, 2016.
[NPL730] Office Action for Chinese Application No. 201580009562.5 dated Jul. 3, 2017.
[NPL734] International Preliminary Report on Patentability for Application No. PCT/US2015/032492 dated Jun. 30, 2017.
[NPL736] Office Action in European Application No. 14746193.3 dated Apr. 19, 2017.
[NPL737] International Preliminary Report on Patentability for Application No. PCT/US2015/016273 dated Feb. 19, 2016.
[NPL747] European Search Report for App. No. 15751391.2 dated Aug. 4, 2017.
[NPL755] European Search Report and supplementary Search Report for App. No. 14865374.4 dated Jun. 12, 2017.
[NPL756] European Search Report and Supplemental Search Report in European Application No. 14865374.4 dated Jun. 12, 2017.
[NPL7] PCT/US2015/020046 International Search Report and Written Opinion dated Jun. 29, 2015.
[NPL81] U.S. Appl. No. 61/480,539 dated Apr. 29, 2011.
[NPL84] U.S. Appl. No. 61/480,535 dated Apr. 29, 2011.
[NPL8] PCT/US2015/020044 International Search Report Written Opinion dated Jun. 30, 2015.
[NPL90] Nedelkov, et. al., Design of buffer exchange surfaces and sensor chips for biosensor chip mass spectrometry, Proteomics, 2002, 441-446, 2(4).
[NPL] European Search Report App 14865374.4, dated Jun. 12, 2017.
Chinese Office Action in App. No. 201580009563.X, dated Mar. 13, 2018.
European Search Report for App. No. 15812081.6, dated Mar. 8, 2018.
European Search Report for App. No. 18153940.4, dated Jun. 12, 2018.
European Search Report for EP 15811439, dated Feb. 15, 2018.
European Search Report for EP App. No. 15810804.3, dated Feb. 15, 2018.
European Search Report for EP App. No. 15811326.6, dated Feb. 14, 2018.
European Search Report for EP App. No. 15811573.3, dated Feb. 15, 2018.
European Search Report for EP App. No. 15812413.1, dated Feb. 2, 2018.
European Search Report in EP 15811454, dated Feb. 15, 2018.
European Search Report in EP 15812559.1, dated Jan. 31, 2018.
Office Action in Japanese Application No. 2016-553344, dated Apr. 24, 2018.
PCT/US2016/030304_IPRP.
PCT/US2016/030319_IPRP.
Search Report for EP App. No. 17203984.4, dated Mar. 29, 2018.
Search Report in EP App. No. 15752771, dated Nov. 22, 2017.

\* cited by examiner

STACKED SORBENT ASSEMBLY

CROSS-REFERENCE TO RELATED APPLICATION

This application is a continuation of U.S. patent application Ser. No. 14/645,394 filed Mar. 11, 2015, which claims benefit of and priority to U.S. Provisional Application No. 62/016,611 filed Jun. 24, 2014, and the disclosures of each of the above-identified applications are hereby incorporated by reference in their entirety.

FIELD OF THE INVENTION

The invention relates to an assembly or array of discrete compartments of sorbent materials, such as a sorbent pouch, wherein the compartments contain at least one sorbent material, and the compartments are constructed such that fluid freely passes through the compartments while the sorbent materials remain inside the compartments.

BACKGROUND

Known dialysate fluid circulation systems and apparatuses have separate housings wherein a first housing has a sorbent material capable of performing a first function such as releasing sodium into dialysate fluid flowing through the first housing, and a second housing has a material capable of performing another function such as binding sodium ions from dialysate fluid flowing through the second housing. However, such systems are not modular and customizable and are usually formed into a single housing design that limits flexibility and the possibility of customized use personalized to a particular patient. Moreover, such sorbent systems are one-size-fits-all and operate using similar amounts of sorbent materials across different treatment sessions regardless of the unique needs or dialysis parameters for a particular patient. Known sorbent systems also do not provide for recharging some or all of the components of a sorbent cartridge that would allow reuse of specific components and enable lower long-term costs for operating such systems, nor ease of manufacturing the separate sorbent housings. Providing for multiple sorbent materials within a single sorbent cartridge, or a single module of a sorbent cartridge, can also be problematic because fine particles in one of the layers can settle in and intermix into the other layers.

As such, there is a need for a system whereby the individual layers of sorbent materials within a sorbent cartridge can be kept separate while maintaining a unitary sorbent cartridge design. There is also a need for sorbent materials to be reusable or optionally detachable from and re-attachable in a modular and interchangeable design to allow for any one of disposal, recycling, recharging of sorbent material, or customized or personalized use of the sorbent materials. There is also a need for a sorbent packaging system that can allow dialysate to freely move into and out of the packaging while keeping the sorbent material inside the packaging. There is a need for a sorbent packaging made from a porous material that keeps the different sorbent materials separated from each other without requiring additional housings. Similarly, there is a need for a sorbent cartridge having a separation of materials within the sorbent cartridge to allow for isolation of those materials.

There is also a need for a sorbent packaging system, assembly or array, providing for isolation of one or more sorbent materials to allow for cheaper or non-reusable materials to be discarded, while more expensive and reusable materials are recharged. As such, there is a need for a sorbent partition such as a sorbent pouch or a system of sorbent pouches that can allow dialysate to freely move into and out of the sorbent pouch while keeping the sorbent material inside. There is a need for a sorbent pouch that keeps the different sorbent materials separated from each other, but still allows the sorbent materials to be used together in a customizable manner. There is also a need for facilitating ease of packaging and shipping using a modular interchangeable system to house sorbent materials. There is the need for providing an option for allowing sub-vendors to manufacture sorbent housing or separate assembly line fill production facilities from one another. There is also a need for providing a customized sorbent system wherein different layers of sorbent materials can be used together wherein each sorbent pouch is modular and interchangeable. There is also a need for reducing final assembly steps required in preparing a dialysis system for use. To combat counterfeiting, there is a need for isolating individual vendors from a sorbent manufacturing process wherein specific sorbent materials used for dialysis can be pre-filled separately. There is also a need for pre-filling a component housing sorbent materials at precise quantities to avoid user error.

SUMMARY OF THE INVENTION

The invention relates to a sorbent assembly. In any embodiment of the invention, the sorbent assembly can comprise two or more sorbent pouches stacked in series. The two or more sorbent pouches can be formed from a porous material wherein the sorbent pouches contain at least one sorbent material. The porous material can allow fluid to pass through the sorbent pouches.

In any embodiment of the invention, the porous material can allow fluid to pass through the sorbent pouches but substantially retains the at least one sorbent material in the sorbent pouches.

In any embodiment of the invention, the porous material can allow fluid to pass through the sorbent pouches but can retain at least 98% by weight of the at least one sorbent material in the sorbent pouches. In any embodiment of the invention, the porous material can allow fluid to pass through the sorbent pouches but can retain anywhere from at least 70%, 75%, 80%, 85%, 90%, 92%, 93%, 94%, 95%, 96%, or 97% by weight of the at least one sorbent material in the sorbent pouches.

In any embodiment of the invention, any one of the sorbent pouches can contain sorbent materials selected from the group consisting of activated carbon, hydrous zirconium oxide, zirconium phosphate, ion-exchange resin, alumina, urease, and combinations thereof.

In any embodiment of the invention, the sorbent material can be urease, and the porous material can allow fluid containing dissolved urease to pass through the sorbent pouches.

In any embodiment of the invention, the sorbent pouches can be attached to each other via any one of an adhesive, sewn stitch, mechanical engagement, and combinations thereof.

In any embodiment of the invention, the sorbent pouch can be constructed from a porous material selected from any one of bolting cloth, porous polymer, porous metal, cotton, ashless filter paper, Dacron and polyethylene terephthalate. In any embodiment of the invention, the sorbent pouch can contain glass beads.

In any embodiment of the invention, the sorbent assembly can comprise at least one sensor in fluid communication with fluid flowing out from at least one of the sorbent pouches, the sensor being capable of sensing the presence and/or concentration of at least one compound in the fluid.

In any embodiment of the invention, at least one sorbent pouch can be reusable.

In any embodiment of the invention, the reusable sorbent pouch can contain a sorbent material that can be recharged.

In any embodiment of the invention, the reusable sorbent pouch can contain a sorbent material that is disposable.

In any embodiment of the invention, at least one sorbent pouch can be constructed of a material that is impregnated with an antimicrobial substance and/or anticoagulant.

In any embodiment of the invention, the sorbent assembly can further comprise a sorbent assembly shell. The sorbent pouch can have an engagement member capable of cooperatively engaging a groove disposed on an interior surface of the sorbent assembly shell such that in order for the sorbent pouch to fit into the sorbent assembly shell, the engagement member is aligned with the groove on the interior wall of the sorbent assembly shell.

In any embodiment of the invention, the at least one sorbent materials can be separated by a separator.

In any embodiment of the invention, at least one sorbent pouch can have a shape selected from the group comprising a rectangle, a square, a disc, a triangle, an octagon, or a polygon.

In any embodiment of the invention, at least one sorbent pouch can be opened and resealed.

In any embodiment of the invention, at least one sorbent pouch can further comprise an o-ring seal member.

In any embodiment of the invention, at least one sorbent pouch can comprise a double layer of material.

In any embodiment of the invention, at least one sorbent pouch can have a planar base with upwardly extending walls connecting to a planar top wherein the walls can be constructed from a rigid, fluid impermeable material.

In any embodiment of the invention, the base and top can be circular and the upwardly extending walls can slope inward to an axis of the sorbent pouch wherein the top can have a smaller surface area than the base or the upwardly extending walls can slope outward from the axis of the sorbent pouch wherein the top can have a larger surface area than the base.

In any embodiment of the invention, the base and top can be rectangular, having four upwardly extending walls sloping inward to an axis of the sorbent pouch wherein the top can have a smaller surface area than the base or four upwardly extending walls sloping outward from the axis wherein the top has a larger surface area than the base.

In any embodiment of the invention, the top can have an engagement member disposed upwardly from the top surface of the sorbent pouch.

In any embodiment of the invention, the base can have a receiving groove disposed on the base for receiving an engagement member.

In any embodiment of the invention, the sorbent pouches can be individually colored or marked so as to distinguish a sorbent pouch containing one sorbent material from a sorbent pouch containing a different sorbent material.

In any embodiment of the invention, the coloring or marking can correspond to an intended order of sorbent pouches within the sorbent assembly.

In any embodiment of the invention, the planar base of the at least one sorbent pouch can have an engagement member disposed downwardly from a bottom surface of the sorbent pouch.

In any embodiment of the invention the planar top of the at least one sorbent pouch can have a receiving groove disposed on a top surface of the sorbent pouch for receiving an engagement member.

In any embodiment of the invention, the planar tops of each of the sorbent pouches can have engagement members disposed upwardly from a top surface of each sorbent pouch, wherein the planar bases of each sorbent pouch can have a receiving groove disposed on a bottom surface of each sorbent pouch for receiving an engagement member; wherein the sorbent assembly can comprise a sorbent pouch containing urease, a sorbent pouch containing zirconium phosphate and optionally at least one sorbent pouch containing another sorbent material; and wherein the engagement member on the planar top of the sorbent pouch containing urease and the receiving groove on the planar base of the sorbent pouch containing zirconium phosphate can be of a different size than the engagement member and receiving groove on the at least one sorbent pouch containing another sorbent material.

In any embodiment of the first invention, the planar bases of each of the sorbent pouches can have engagement members disposed downwardly from a bottom surface of each sorbent pouch, wherein the planar tops of each sorbent pouch can have a receiving groove disposed on a top surface of each sorbent pouch for receiving an engagement member; wherein the sorbent assembly can comprise a sorbent pouch containing urease, a sorbent pouch containing zirconium phosphate and at least one sorbent pouch containing another sorbent material; and wherein the engagement member on the planar base of the sorbent pouch containing urease and the receiving groove on the planar top of the sorbent pouch containing zirconium phosphate can be of a different size than the engagement member and receiving groove on the at least one sorbent pouch containing another sorbent material.

In any embodiment of the invention, the sorbent assembly can have at least one sorbent pouch with urease; wherein the sorbent pouch containing urease is constructed of a porous material allowing dissolved urease to pass through the sorbent pouch.

In any embodiment of the invention, the assembly can have one sorbent pouch that contains alumina and another sorbent pouch that contains urease wherein the sorbent pouch containing urease is constructed of a porous material that allows fluid to pass through the sorbent pouch and also allows dissolved urease to pass through the sorbent pouch, and wherein the sorbent pouch containing urease is constructed of a porous material that allows fluid and dissolved urease to pass through the sorbent pouch, but substantially retains the alumina. In any embodiment of the invention, the sorbent pouch containing alumina can retain at least 98% by weight of the alumina.

In any embodiment of the invention, each of the two or more sorbent pouches can comprise sidewalls having a thickness different from the sidewall thicknesses of the other sorbent pouches, such that the two or more sorbent pouches can have differing interior diameters.

In any embodiment of the invention, each sorbent pouch can have a sidewall thickness greater than that of the previous sorbent pouch in series.

In any embodiment of the invention, each of the two or more sorbent pouches can have differing exterior diameters.

In any embodiment of the invention, each sorbent pouch can have an exterior diameter smaller than that of the previous sorbent pouch in series.

In any embodiment of the invention, the two or more sorbent pouches can each contain one or more annular ring. In any embodiment of the invention, the one or more annular ring can be constructed from a fluid impermeable substance, and the one or more annular ring can be disposed on the interior circumference of each of the two or more sorbent pouches and can extend radially into the center of each of the two or more sorbent pouches.

In any embodiment of the invention, the annular ring can have a cross-sectional shape selected from the group comprising circular, triangular, and rectangular.

Any of the features disclosed as being part of the invention can be included in the invention, either alone or in combination.

DETAILED DESCRIPTION OF THE INVENTION

Figure 1:
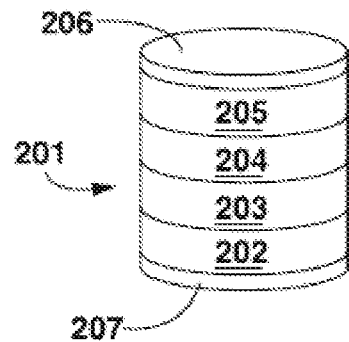
FIG. 1 is a perspective view of a sorbent cartridge containing sorbent pouches of activated carbon, hydrous zirconium oxide, urease, alumina, and zirconium phosphate.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

An "adhesive" is any substance known in the art for use in affixing one surface to another surface, or to seal two surfaces together.

"Ammonia detector" refers to any apparatus that is capable of detecting the presence or concentration of ammonia or ammonium ions in a fluid.

An "annular ring" is a ring having a substantially circular shape. The cross-section of the ring may be rectangular, triangular, round, or any other known shape. The ring may be constructed of any rigid or semi-rigid material, and may be adhered to the inner surface of a sorbent pouch by any means known in the art. An annular ring may also be an "o-ring."

An "axis of the sorbent pouch" describes an imaginary line running vertically down the center of the sorbent pouch, situated in the center of the surface of the sorbent pouch when viewed from the top perspective.

The term "cartridge" refers to any container designed to contain a powder, fluid, or gas made for ready connection to a device, structure, system, flow path or mechanism. The container can have one or more compartments. Instead of compartments, the container can also be comprised of a system of two or more modules connected together to form the cartridge wherein the two or more modules once formed can be connected to a device, structure, system, flow path or mechanism.

A "circular shape" describes a sorbent pouch constructed in a generally round shape having the form of a circle. This term is not intended to limit the shape of the sorbent pouch to any particular size or dimensions, and may encompass oval or oblong configurations as well.

A "compartment" means a part or a space designated, defined, marked or partitioned off from a structure. For example, a urease compartment in a sorbent cartridge is a space defined within the sorbent cartridge containing urease, including urease immobilized to an immobilizing sorbent material, such as alumina. Optionally, the compartment can be in selected fluid communication with other compartments or modules of the sorbent system. The compartment can be physically separated or marked off without a physical barrier.

The term "comprising" includes, but is not limited to, whatever follows the word "comprising." Thus, use of the term indicates that the listed elements are required or mandatory but that other elements are optional and may or may not be present.

The term "consisting of" includes and is limited to whatever follows the phrase "consisting of." Thus, the phrase indicates that the limited elements are required or mandatory and that no other elements may be present. The term "consisting essentially of" includes whatever follows the term "consisting essentially of" and additional elements, structures, acts or features that do not affect the basic operation of the apparatus, structure or method described.

The term "detachable" or "detached" relates to any component of the present invention that can be separated from a system, module, sorbent pouch, cartridge or any component of the invention. "Detachable" can also refer to a component that can be taken out of a larger system with minimal time or effort. In certain instances, the components can be detached with minimal time or effort, but in other instances can require additional effort. The detached component can be optionally reattached to the system, module, cartridge or other component. A detachable module can often be part of a reusable module.

"Dialysate" is the fluid that passes through the dialyzer on the side of the dialysis membrane that is opposite to the fluid (e.g. blood) that is being dialyzed.

A "disc-like shape" describes a sorbent pouch forming a flat, circular shape, as in a compressed cylinder. This definition is not intended to limit the dimensions or radius of the sorbent pouch, and may therefore encompass discs having an oval shape, and discs of any radial width or thickness.

"Disposable" refers to a component that is to be removed from the system and not reused.

A "double layer of material" describes a second layer of material of the same or smaller area than the primary layer of material, disposed on the surface of the primary layer of material forming a surface of a sorbent pouch. The material used to form the double layer can be the same or different from the material forming the primary layer. Any rigid or flexible porous material known in the art is contemplated.

An "elastomer" or "elastomeric material" is a material comprising a polymer having high elasticity, such that the material may be easily stretched and shaped to be adapted to an internal cavity defined by a sorbent cartridge.

"Engagement members" allow compartments to cooperatively engage. In certain embodiments, these engagement members may be clasps or latches. In one embodiment, an engagement member allows for coupling of a top portion and a bottom portion of a sorbent pouch that can be opened and resealed.

"Flow" refers to the movement of a fluid or gas.

A "fluid" is a liquid substance optionally having a combination of gas and liquid phases in the fluid. Notably, a liquid, as used herein, can therefore also have a mixture of gas and liquid phases of matter.

The term "fluid communication" refers to the ability of fluid or gas to move from one component or compartment to another within a system or the state of being connected, such that fluid or gas can move by pressure differences from one portion that is connected to another portion.

A "fluid impermeable material" is any material through which fluid cannot pass.

The term "fluidly connectable" refers to the ability of providing for the passage of fluid or gas from one point to another point. The two points can be within or between any one or more of compartments, modules, systems, components, and rechargers, all of any type.

A "geometric shape" refers any geometric shape in Euclidean and other geometries such as a rectangle, disc, triangle, or polygon inter alia. In reference to a sorbent pouch as described in the invention, the geometric shape can refer to one or more side of the sorbent pouch wherein a rectangular sorbent pouch can be generally constructed to have a rectangular shape at least on one side to form a porous sealed bag.

"Immobilized," as used to refer to a chemical component, refers to a configuration wherein a chemical component is held in place by some force. The force may be provided by absorption, adsorption, adhesion, or any other method for the chemical to be held in place.

The term "immobilizing sorbent material" refers to the process of a sorbent material being placed onto another material, such that the sorbent material is held in place by some force. The force may be provided by absorption, adsorption, adhesion, or any other method for the chemical to be held in place.

The term "impregnated" describes any process known to a person of ordinary skill in the art by which a material may be caused to absorb or be saturated with a substance. In one embodiment, the material forming a sorbent pouch may be impregnated with an anticoagulant, such that the surface of the sorbent pouch absorbs the anticoagulant.

The term "in-part" describes a portion up to and including one hundred percent. For example, a component formed in-part by a material means that the material forms at least some portion of the component, and that the material may form up to the entire component.

"Mechanical engagement" describes any means known in the art of physically attaching two components together, for example by use of a latch and flange, or male and female interlocking components.

"Module" refers to a discreet component of a system. Each of the modules can be fitted to each other to form a system of two or more modules. Once fitted together, the modules can be in fluid connection and resist inadvertent disconnection. A single module can represent a cartridge to be fitted to a device or mechanism if the module is designed to contain all the necessary components for an intended purpose such as a sorbent for use in dialysis. In such a case, the module can be comprised of one or more compartments within the module. Alternatively, two or more modules can form a cartridge to be fitted to a device or mechanism where each module individually carries separate components but only when connected together contain in summation all the necessary components for an intended purpose such as a sorbent for use in dialysis. A module can be referred to as a "first module," "second module," "third module," etc. to refer to any number of modules. It will be understood that the designation of "first," "second," "third," etc. does not refer to the respective placement of the module in the direction of fluid or gas flow, and merely serves to distinguish one module from another unless otherwise indicated.

The term "non-reusable" refers to a component that cannot be reused in the component's current state. In certain instances, the term non-reusable can include the concept of being disposable, but is not necessarily limited to just being disposable.

An "o-ring seal member" is a mechanical gasket having a ring shape; it is a loop of elastomer or other suitable material known in the art with a round cross-section, designed to be seated in a groove and compressed during assembly between two or more parts, creating a seal at the interface. In one embodiment, an o-ring seal member may be used to seal the interface between a sorbent pouch and a sorbent cartridge such that fluid is directed through, rather than around, the sorbent pouch.

The terms "pathway," "conveyance pathway," "fluid flow path," and "flow path" refer to the route through which a fluid or gas, such as dialysate or blood, travels.

A "planar top" or "planar base" is a surface perpendicular to the axis of the urease pouch culminating at the uppermost portion of the upwardly extending walls of a urease pouch, or a flat surface culminating at the bottommost portion of the downwardly extending walls of a urease pouch, respectively. The planar top may be any geometric shape and dimensions complementary to the upwardly extending walls of the urease pouch, for example round, square, triangular or rectangular. A circular planar top or planar base is a flat surface having a circular shape, while a rectangular planar top or planar base is a flat surface having a square or rectangular shape.

A "porous material" may describe any suitable porous material known in the art from which a sorbent pouch may be constructed. For example, the porous material can include, but is not limited to, bolting cloth, porous polymer, porous metal, cotton, ashless filter paper, Dacron and polyethylene terephthalate. The porous material chosen for individual sorbent pouches may be selected based upon specific porosity in view of the sorbent material to be contained within the sorbent pouch.

A "porous structure" describes a sorbent pouch being formed of a porous material, wherein the sorbent pouch can be manipulated to fit an internal cavity defined by a sorbent cartridge.

"Recharging" refers to the process of treating spent sorbent material to restore the functional capacity of the sorbent material, so as to put the sorbent material back into a condition for reuse or for use in a new dialysis session. In some instances, the total mass, weight and/or amount of "rechargeable" sorbent materials remain the same. In other embodiments, the total mass, weight and/or amount of "rechargeable" sorbent materials may change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged." Recharging of rechargeable sorbent materials is not the same as replenishing of a particular sorbent material such as urease.

"Reusable" refers in one instance to a material that can be used more than one time, possibly with treatment or recharging of the material between uses. Reusable may also refer to a cartridge that contains a material that can be recharged by recharging the material(s) contained within the cartridge.

A "rigid structure" describes a sorbent pouch being formed of inflexible material such that the sorbent pouch cannot be manipulated and reshaped to be adapted to an internal cavity defined by a sorbent cartridge, but instead maintains its shape.

A "semi-rigid structure" describes a sorbent pouch having surfaces that can be flexed, but that are substantially rigid unless force is applied to cause the surfaces to flex.

A "sensor" is a component capable of determining the states of one or more variables in a system. In one embodiment, a sensor may be capable of sensing the presence and/or concentration of at least one compound in the fluid flowing through at least one sorbent pouch, using any means known in the art.

A "separator" is a layer of flexible or rigid material positioned within a sorbent pouch that divides the sorbent pouch into top and bottom portions, such that sorbent materials housed in the top and bottom portions, respectively, do not come in contact with each other. The separator is formed of a porous material such that spent dialysate or other fluid may flow between the top and bottom portions of the sorbent pouch through the separator, but such that the sorbent materials housed in the top and bottom portions of the sorbent pouch cannot pass through the separator.

A "sorbent assembly shell" is an empty sorbent cartridge housing into which the stacked sorbent assembly is inserted.

"Sorbent cartridge" refers to a cartridge that can contain one or more sorbent materials. The cartridge can be connected to a dialysis flow path. The sorbent materials in the sorbent cartridge are used for removing specific solutes from solution, such as urea. The sorbent cartridge can have a single compartmental design wherein all sorbent materials necessary for performing dialysis are contained within the single compartment. Alternatively, the sorbent cartridge can have a modular design wherein the sorbent materials are dispersed across at least two different modules, which can be connected to form a unitary body. Once the at least two modules are connected together, the connected modules can be referred to as a sorbent cartridge, which can be fitted to a device or mechanism. When a single module contains all the sorbent materials necessary for performing dialysis, the single module can be referred to as a sorbent cartridge.

"Sorbent materials" are materials capable of removing specific solutes from solution, such as urea or urea byproducts.

The term "sorbent pouch" refers to a structure that contains at least one sorbent material, and is constructed from a material that can allow fluid to freely pass through the sorbent pouch while substantially retaining the sorbent material inside the pouch.

A "sewn stitch" is a method of sealing two surfaces together using a needle and a thread composed of any material known in the art.

"Spent dialysate" is a dialysate contacted with blood through a dialysis membrane and contains one or more impurities, or waste species, or waste substance, such as urea.

A "square" or "rectangular" shape describes a sorbent pouch having four edges and four angles. This description is not intended to limit the size and dimensions of the sorbent pouch, and may therefore encompass sorbent pouches having corners with angles greater than or less than ninety degrees, and with edges of differing lengths with respect to each other.

The term "substantially," is used in conjunction with a term to describe a particular characteristic. For example, as used in the phrase "substantially retains the at least one sorbent material in the sorbent pouches," the term describes the ability to retain a sorbent material or particles characterized by an average pore diameter such that a significant amount of the material or particles are retained within the sorbent pouch.

A "threaded fitting" is a fitting for connecting two components wherein the male portion has a helical ridge wrapped around a cylinder, and the female portion is a cylindrical hole with internal helical ridges so that when the male portion is screwed into the female portion the two components are locked together.

A "triangular shape" describes a sorbent pouch having three edges and three corners, wherein the edges and corners may vary in length and degree individually and with respect to each other.

A "twist-lock fitting" is a fitting for connecting two components wherein the male portion of the fitting contains a head with a length exceeding its width, the female portion of the fitting is a hole with a length that exceeds its width and is larger than the male portion, so that when the male portion is inserted into the female portion and either portion is twisted the two components become locked together.

"Upwardly extending walls" describe the surfaces extending radially outward from the top and bottom surfaces of a sorbent pouch. For example, in a sorbent pouch having a disc-like shape, the circular top and bottom portions of the sorbent pouch are connected by the rounded upwardly extending wall of the sorbent pouch. The upwardly extending walls may be of any shape or dimensions complementary to the corresponding top and bottom portions of the sorbent pouch. In the case of a triangular shaped sorbent pouch, the upwardly extending walls would extend from a bottom portion of the sorbent pouch and culminate at a vertex, in the absence of a top portion.

Stacked Sorbent Assembly

This invention is drawn to a sorbent cartridge comprising a stacked assembly of sorbent pouches. One non-limiting embodiment of the invention is shown in FIG. 1. The sorbent cartridge 201 can comprise a sorbent pouch containing activated carbon 202, a sorbent pouch containing hydrous zirconium oxide 203, a sorbent pouch containing alumina/urease 204, and a sorbent pouch containing zirconium phosphate 205. In any embodiment of the invention, the alumina and urease can occupy separate sorbent pouches (not shown). Spent dialysate can enter through the bottom surface 207 of the sorbent cartridge 201, and flow through each of the sorbent pouches 202-205 sequentially, and then flow out of the sorbent cartridge 201 through the top surface 206 of the sorbent cartridge 201. In this way, the spent dialysate can come into contact with each sorbent material layer, while each sorbent material layer is kept separate from each of the other layers. One skilled in the art will understand that, in any embodiment of the invention, the sorbent pouches may be arranged in alternate orders and still be within the scope of the invention. For example, the first sorbent pouch 202 may contain activated carbon, the second sorbent pouch 203 may contain alumina/urease, the third sorbent pouch 204 may contain hydrous zirconium oxide, and the fourth sorbent pouch 205 may contain zirconium phosphate. In any embodiment of the invention, the first sorbent pouch 202 may contain activated carbon, the second sorbent pouch 203 may contain alumina/urease, the third sorbent pouch 204 may contain zirconium phosphate and the fourth sorbent pouch 205 may contain hydrous zirconium oxide. The precise order of the sorbent pouches within the sorbent cartridge 201 is not critical to the invention so long as a sorbent pouch containing zirconium phosphate is located downstream of the sorbent pouch containing alumina/urease. In any embodiment of the invention, a sorbent pouch can contain multiple sorbent materials, either arranged in layers or alternatively intermixed within the sorbent pouch. In any sorbent pouch, glass beads can be incorporated into the sorbent material to facilitate flow. Additionally, any number of sorbent pouches arranged sequentially in the sorbent cartridge is envisioned.

Figure 2:
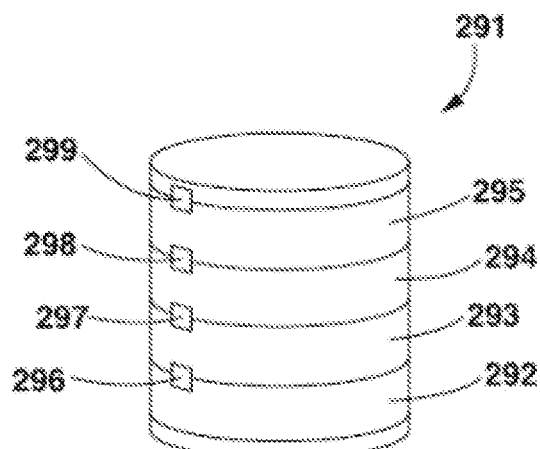
FIG. 2 perspective view of a sorbent cartridge containing sorbent pouches of activated carbon, hydrous zirconium oxide, urease, alumina, and zirconium phosphate with sensors placed within the sorbent cartridge to monitor the content of the spent dialysate.

In any embodiment of the invention, sensors may be positioned after or between the sorbent pouches and optionally inside a sorbent cartridge housing the sorbent pouches, to ensure that fluid is properly passing through the sorbent pouch and that the sorbent material within the sorbent pouch is properly removing or converting the toxins present in the spent dialysate. For example, as shown in FIG. 2, a sorbent cartridge 291 can comprise a sorbent pouch containing activated carbon 292, a sorbent pouch containing hydrous zirconium oxide 293, a sorbent pouch containing alumina/urease 294, and a sorbent pouch containing zirconium phosphate 295. The sorbent pouches can be placed in any order, so long as the sorbent pouch containing zirconium phosphate is located downstream of the sorbent pouch containing alumina/urease. In any embodiment of the invention, the alumina and urease can occupy separate sorbent pouches (not shown). For example, the first sorbent pouch 292 can contain activated carbon, the second sorbent pouch 293 can contain alumina/urease, the third sorbent pouch 294 can contain hydrous zirconium oxide and the fourth sorbent pouch 295 can contain zirconium phosphate. In any embodiment of the invention, the first sorbent pouch 292 can contain alumina/urease, the second sorbent pouch 293 can contain hydrous zirconium oxide, the third sorbent pouch 294 can contain zirconium phosphate and the fourth sorbent pouch 295 can contain activated carbon. Further, any sorbent pouch can contain multiple sorbent materials, either arranged in layers or intermixed as described above, thus allowing for the use of less sorbent pouches. A sensor 296 can be placed after the sorbent pouch containing activated carbon 292 to test the spent dialysate for toxins that are normally removed by activated carbon, such as β-2 microglobulin or creatinine. Another sensor 297 can be deployed after the sorbent pouch containing hydrous zirconium oxide 293 to test the spent dialysate for the presence of phosphates or fluoride ions. A third sensor 298 can be deployed after the alumina/urease containing sorbent pouch 294 to test for the presence of urea. A fourth sensor 299 can be deployed after the zirconium phosphate containing sorbent pouch 295 to test for the presence of ammonia. Although FIG. 2 shows four sensors being used, the present invention contemplates using any number of sensors, including more or less than four. The presence of additional compounds that may be present in spent dialysate can be tested, and the presence of all of the compounds described above need not be tested. In any embodiment of the invention, the sensors can be conductivity sensors.

In any embodiment of the invention, the sorbent pouches may be made with fluid impermeable side walls. The side walls may be made out of metal or any other material known in the art, such as plastic. In any embodiment of the invention where the top and bottom layers of the sorbent pouches are made out of a fluid permeable substance, such as fabric, the side walls of the sorbent pouches may be made out of a fluid impermeable substance. In any embodiment of the invention, the sorbent pouches themselves may connect together directly, eliminating the need for an external housing. In any embodiment of the invention, the sorbent pouches themselves can form the sorbent cartridge. In any embodiment of the invention, shown in FIG. 3, the top and bottom layers of the sorbent pouch can have a means for connecting to another sorbent pouch. For example, first sorbent pouch 301 can have engagement members 303 on the top surface of the sorbent pouch 301. Second sorbent pouch 302 can have engagement members 304 on the bottom surface of the sorbent pouch 302. Engagement members 303 of the first sorbent pouch 301 and engagement members 304 of the second sorbent pouch 302 can connect together in any known fashion to seal the two sorbent pouches together. O-ring 305 on the first sorbent pouch 301 and o-ring 306 on the second sorbent pouch 302 can create a water-tight seal when the two sorbent pouches are connected, eliminating any leaks from the interface. Because the side wall 307 of the first sorbent pouch 301 and the side wall 308 of the second sorbent pouch 302 are impermeable to fluid, there will be no leakage from the sides of the structure either. In this way, the sorbent pouches of the invention can fit together without the need for containment in an external sorbent cartridge.

Figure 3:
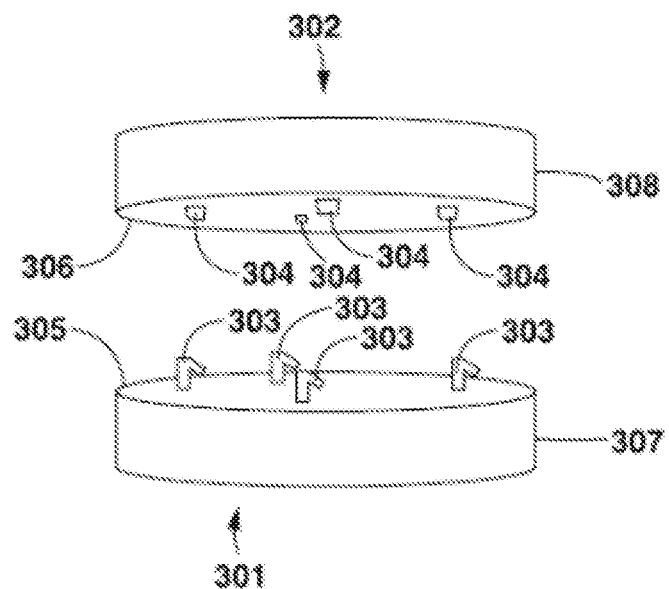
FIG. 3 is a perspective view of two sorbent pouches with the ability to connect directly together.

The engagement members 303 and 304 can be constructed in any known fashion to create a sealed structure. In FIG. 3, they are shown as a twist lock fitting. The engagement members 303 can fit into the holes serving as engagement members 304. When the sorbent pouches are twisted, the engagement members 303 can turn relative to the holes 304. This creates a construct wherein the top portion of engagement members 303 cannot fit back out of the holes 304. In order to separate the sorbent pouches, one must twist the sorbent pouches back in the opposite direction so that the tops of engagement members 303 can once again fit through the holes 304 and allow easy disengagement. Any other known method of connecting the first sorbent pouch 301 and the second sorbent pouch 302 is contemplated by this invention.

First sorbent pouch 301 can also have engagement members similar to 304 disposed on the bottom surface of the sorbent pouch (not shown) to facilitate the attachment of another sorbent pouch before the first sorbent pouch 301. Similarly, second sorbent pouch 302 can have engagement members similar to 303 disposed on the top surface of the sorbent pouch (not shown) to facilitate the attachment of another sorbent pouch after the second sorbent pouch 302.

In any embodiment of the invention, the engagement members can be configured so as to ensure proper sequencing of the sorbent pouches. For example, a zirconium phosphate sorbent pouch must be placed downstream of a sorbent pouch containing urease to remove the ammonia created by the breakdown of urea in the urease sorbent pouch. The engagement members on the bottom of the zirconium phosphate sorbent pouch and the top of the urease sorbent pouch may be configured so that they can only engage with one another; that is so that the zirconium phosphate sorbent pouch can only be attached immediately downstream of the urease sorbent pouch and the urease sorbent pouch can only be attached immediately upstream from the zirconium phosphate sorbent pouch. In any embodiment of the invention, this can be accomplished by using engagement members for the top surface of the urease sorbent pouch and the bottom surface of the zirconium phosphate sorbent pouch that are of a different size than the engagement members on other sorbent pouches. Alternatively, the individual sorbent pouches may be colored, or marked, to indicate the proper sequencing of sorbent pouches.

In any embodiment of the invention, two or more sorbent pouches containing the same sorbent material can be used. For highly uremic or particularly large patients, more of a given sorbent material may be necessary. In such cases, a second sorbent pouch containing, for example, zirconium phosphate, may be used in the system. This would give the patient twice as much of the sorbent material, allowing the removal of a greater amount of a given toxin or toxins in a single uninterrupted dialysis session.

The stacked assembly of the invention utilizes separate sorbent pouches that contain individual portions of sorbent material, or multiple layers of sorbent material. The sorbent pouches are designed such that spent dialysate or water may pass through the sorbent pouch and into the sorbent material or materials within, and the spent dialysate or water may then pass out of the sorbent pouch, while the sorbent materials remain inside the sorbent pouch.

The sorbent pouches of the invention can be constructed in any shape. For convenience, they are often drawn as circular or disc shaped. However, any of the described embodiments of the invention can be made in any shape, including triangular, rectangular, etc.

Figure 4:
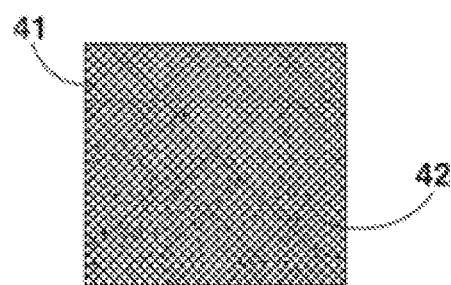
FIG. 4 is a top view of a rectangular sorbent pouch.
Figure 5:
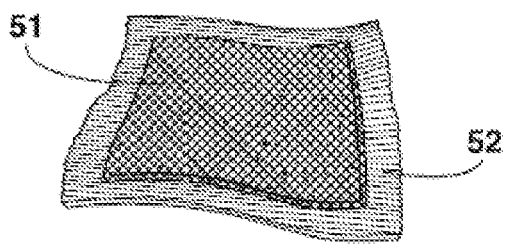
FIG. 5 is a perspective view of a rectangular sorbent pouch.
Figure 6:
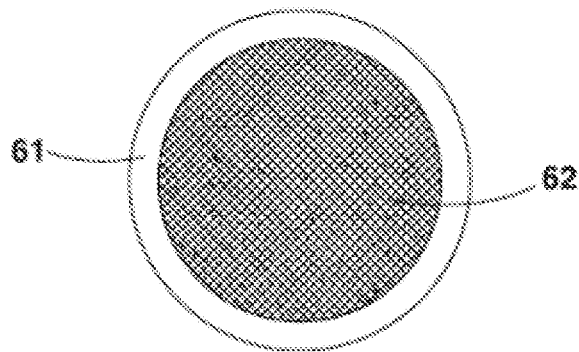
FIG. 6 is a top view of a disc-shaped sorbent pouch.
Figure 7A:
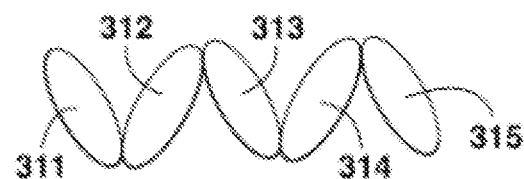
FIG. 7a is a side view of a string of disc-shaped sorbent pouches.
Figure 7B:
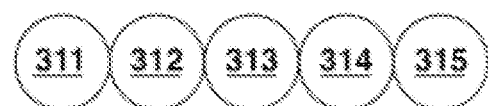
FIG. 7b is a top view of a string of disc-shaped sorbent pouches.
Figure 7C:
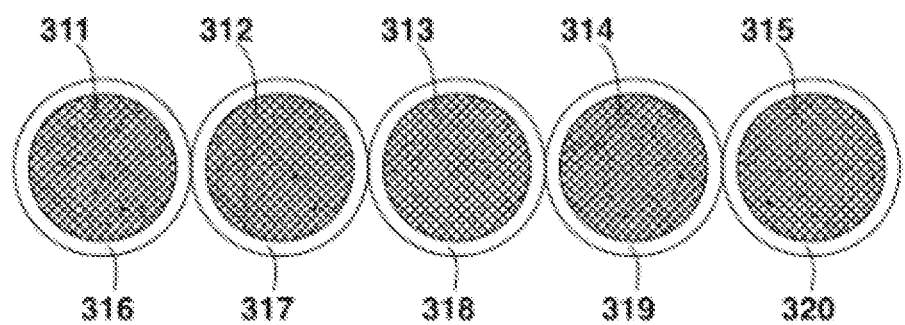
FIG. 7c is a top view of a string of disc-shaped sorbent pouches showing the detail of the outer edges of the sorbent pouches.
Figure 7D:
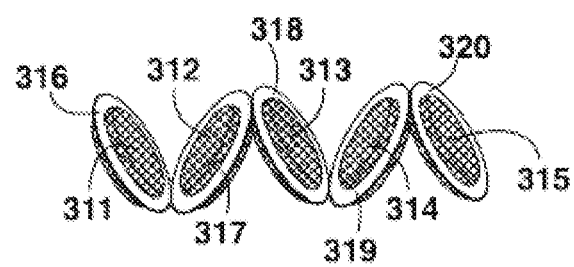
FIG. 7d is a perspective view of a string of disc-shaped sorbent pouches showing the detail of the outer edges of the sorbent pouches.
Figure 8A:
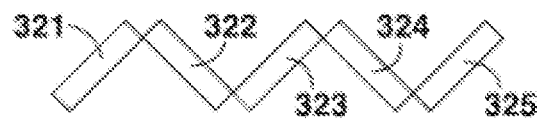
FIG. 8a is a side view of a string of rectangular sorbent pouches.
Figure 8B:
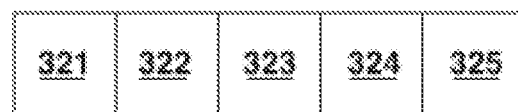
FIG. 8b is a top view of a string of rectangular sorbent pouches.
Figure 8C:
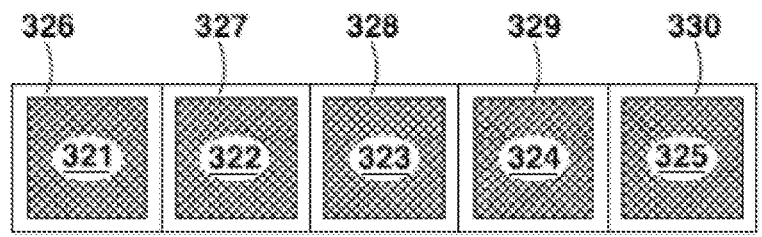
FIG. 8c is a top view of a string of rectangular sorbent pouches showing the detail of the outer edges of the sorbent pouches.

For example, FIGS. 4 and 5 show a rectangular-shaped sorbent pouch 41, whereas FIG. 6 shows a disc shaped sorbent pouch. The sorbent pouches may be constructed of any known material including bolting cloth, porous polymer, porous metal, cotton, ashless filter paper, Dacron, and polyethylene terephthalate as described herein, and each may be constructed in any shape.

In any embodiment of the invention, the sorbent pouches can be configured as shown in FIG. 4. The sorbent pouch 41 can be constructed of a material that can allow fluid to pass through the sorbent pouch 41, but will not allow the sorbent material 42 contained within the sorbent pouch 41 to pass out of the sorbent pouch 41. The sorbent material 42 can be placed loosely in the sorbent pouch 41, allowing the sorbent material 42 to move within the sorbent pouch 41, but not to travel out of the sorbent pouch 41. The sorbent pouch 41 can be made in any size or shape.

FIG. 5 shows a rectangular sorbent pouch embodiment in which the sorbent material is contained in a raised inner portion of the sorbent pouch 51, while the outer perimeter of the sorbent pouch, having a serrated edge 52, is sealed by any means known in the art, including heat or pressure stamping, sewing, or adhesive sealing. The serrated edge 52 of the sorbent pouch may be permanently sealed, or may alternatively be resealable, such that the sorbent pouch may be opened and reclosed. For example, the serrated edge 52 may be sealed with a resealable adhesive, hook and loop fasteners (not shown), or with interlocking ridges (not shown) that may be separated and reclosed by the user. Optionally, a latch member (not shown) may be included on the serrated edge 52 of the sorbent pouch 51 to provide additional strength in sealing the sorbent pouch 51. In any embodiment of the invention, the outer edge may simply be a folded edge. In use, compression from the other materials within a sorbent cartridge can keep the folded edge sealed and the sorbent materials inside the sorbent pouch 51. In any embodiment of the invention, the sorbent pouch 51 may be sealed with drawstrings that when tightened create a seal.

In any embodiment of the invention, the sorbent pouch can be formed from a porous material that allows fluid to pass through the sorbent pouches wherein substantially all of the sorbent material or particles are retained by the porous material. Sorbent materials are generally formed from a solid substance that adsorbs and/or absorbs other substances. In any embodiment of the invention, the porous material can allow fluid to pass through the sorbent pouches but substantially retains the sorbent material in the sorbent pouch. In any embodiment of the invention, the porous material can allow fluid to pass through the sorbent pouches but retain at least 98% by weight of one sorbent material in the sorbent pouch. In any embodiment of the invention, the porous material can allow fluid to pass through the sorbent pouches but can retain anywhere from at least 70%, 75%, 80%, 85%, 90%, 92%, 93%, 94%, 95%, 96%, or 97% by weight of one sorbent material in the sorbent pouch.

In any embodiment of the invention, the pore size of one or more of the sorbent pouches may be large enough so that the sorbent material can leave the sorbent pouch. For example, a sorbent pouch containing solid urease may be made with a pore size large enough to allow the urease to travel out of the sorbent pouch. The urease in any embodiment of the invention can be dissolved by the fluid as it passes through the sorbent pouch during priming of the sorbent cartridge prior to dialysis, and the urease can exit the sorbent pouch. The urease in solution can then contact a sorbent pouch containing immobilized alumina, where the urease will become bound to the alumina in the alumina sorbent pouch. Alternatively, the sorbent cartridge can contain a sorbent pouch containing alumina, and a solution of urease can be injected into the flow path before the sorbent cartridge. The urease solution can enter the sorbent pouch containing alumina, where the urease will become bound to the alumina in the alumina sorbent pouch.

However, in any embodiment of the invention, it may be desirable to retain the dissolved urease in the sorbent pouch and as such the sorbent pouch is constructed from a material that substantially retains the urease within the sorbent pouch. In any embodiment of the invention, the sorbent assembly can comprise two or more sorbent pouches stacked in series.

The size of the sorbent pouches is flexible. Because different amounts of each sorbent material may be required for a dialysis session, the sorbent pouches of the present invention may be in multiple sizes. In any sorbent pouch, glass beads can be incorporated into the sorbent material to facilitate flow.

The sorbent pouches may be constructed of a flexible or rigid porous material. The porous material can be selected from any non-toxic material suitable for the intended use in a dialysis wherein the material can allow fluid to pass through the material yet substantially retains the sorbent material in the sorbent pouch. The porous material can be selected from the materials having the appropriate porosity, strength and durability. In any embodiment of the invention, the flexible material can allow fluid to pass through the sorbent pouches but can retain at least 98% by weight of one sorbent material in the sorbent pouch. In any embodiment of the invention, the porous material can allow fluid to pass through the sorbent pouches but can retain anywhere from at least 70%, 75%, 80%, 85%, 90%, 92%, 93%, 94%, 95%, 96%, or 97% by weight of one sorbent material in the sorbent pouch. When the material is selected for use with urease, alumina may also be provided in the sorbent pouch. Because the alumina will adsorb the urease, and keep the urease from flowing out of the sorbent pouch, the porous material need only substantially retain the alumina.

In any embodiment of the invention, the sorbent pouches may be constructed out of both a flexible and a rigid material. For example, the top and bottom of the sorbent pouch may be constructed from a flexible material, while the sides of the sorbent pouch may be constructed from a rigid material. In any embodiment of the invention, the sorbent pouches can be made out of a material such as a porous polymer. The polymer may be made porous by creating small holes or pores in an otherwise solid polymer material. The polymer may be constructed from polyethylene terephthalate, high density polyethylene, low density polyethylene, polyvinyl chloride, polypropylene, polystyrene, or any other polymer known in the art. In any embodiment of the invention where the sorbent pouch is made of fabric, the weave of the fabric can have a specified porosity suitable for use with the sorbent material described herein for the intended use of dialysis. The pores of the sorbent pouch material must be large enough to allow the spent dialysate to freely travel into and out of the sorbent pouch, while at the same time must be small enough to keep the particles of the sorbent material inside the sorbent pouch. For this reason, sorbent pouches with different pore or mesh sizes can be utilized for different material layers. In any embodiment of the invention, the sorbent pouch may be made out of a natural fiber, such as cotton. In any embodiment of the invention, the sorbent pouch may be constructed from ashless filter paper. The sorbent pouches may also be constructed out of a synthetic material such as Dacron, or polyethylene terephthalate.

In any embodiment of the invention, multiple sorbent pouches may be connected as a string of sorbent pouches, as shown in FIGS. 7a, 7b, 7c, 7d, 8a, 8b and 8c. The individual sorbent pouches 311-315 in the case of disc shaped sorbent pouches, and 321-325 in the case of rectangular sorbent pouches, may be permanently or separably connected at their outer edges 316-320 in the case of disc shaped sorbent pouches or 326-330 in the case of rectangular sorbent pouches, by any means known in the art, including by perforations in the material forming the outer edges 316-320 or 326-330. The individual sorbent pouches comprising the string of sorbent pouches may be composed of the same material; may be composed of different materials such that each sorbent pouch in the string of sorbent pouches is composed of a different material; or may be composed of different materials such that some sorbent pouches in the string of sorbent pouches are composed of the same material, while others are composed of differing materials, and are arranged in a random or repeating pattern. The materials of which the individual sorbent pouches are composed may be selected with particularity to the sorbent material housed inside the sorbent pouch. For example, sorbent pouches containing activated carbon may require a larger mesh to prevent the larger particles from escaping the sorbent pouch. By contrast, sorbent pouches containing hydrous zirconium oxide may require a smaller mesh to prevent the smaller particles from escaping the sorbent pouch. Any combination of sorbent pouch materials and mesh sizes among the string of sorbent pouches, and any number of individual sorbent pouches making up the string of sorbent pouches, is envisioned. Additionally, the sorbent pouches may be constructed in any shape, including but not limited to, rectangular or circular.

Figure 9A:
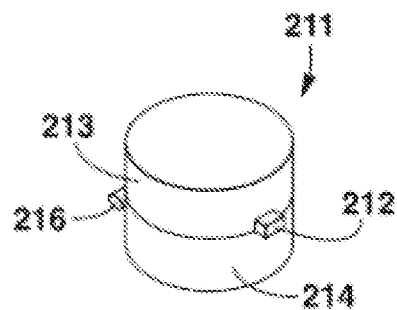
FIG. 9a is a perspective view of a sorbent pouch having the ability to open and reclose via a hinge and a latch member.
Figure 9B:
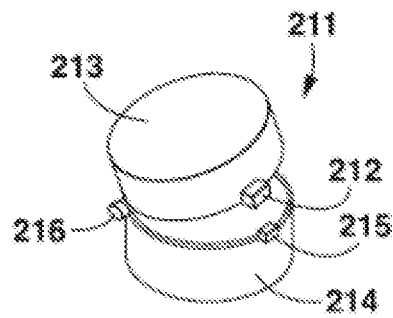
FIG. 9b is a perspective view of a sorbent pouch in an open state.

In any embodiment of the invention, the sorbent pouches of the present invention may be designed so that they can be opened, as shown in FIGS. 9a and 9b. Top portion 213 of the sorbent pouch 211 and bottom portion 214 of the sorbent pouch 211 may be connected by a hinge 216 and a latch member 212. When latch member 212 on the top portion 213 of sorbent pouch 211 is engaged with flange 215 on bottom portion 214 of the sorbent pouch 211, the top portion 213 of the sorbent pouch 211 can be firmly sealed to the bottom portion 214 of the sorbent pouch 211. When latch member 212 of the sorbent pouch 211 is disengaged from flange 215, top portion 213 can pivot on hinge 216 to separate from bottom portion 214. The sorbent material (not shown) within the sorbent pouch 211 can then be removed in order to be discarded or recharged. The sorbent pouch 211 itself may be reused. The sorbent pouch 211 can be closed as shown in FIG. 9b by pivoting the top portion 213 of the sorbent pouch 211 so that top portion 213 and bottom portion 214 meet, and reengaging latch member 212 on the top portion 213 of the sorbent pouch 211 with flange 215 on the bottom portion 214 of the sorbent pouch 211. Any type of connection between the top portion 213 and bottom portion 214 of the sorbent pouch 211 is contemplated by this invention. For example, the top portion of the sorbent pouch may include multiple latches in the absence of a hinge member (not shown), while the bottom portion of the sorbent pouch can include engagement members. When the top portion is placed onto the bottom portion and twisted, the latches can engage the engagement members, creating a connection that can be resistant to inadvertent opening. In order for the connection to be broken, the top portion of the sorbent pouch can be twisted in the opposite direction, allowing the two portions to separate.

In any embodiment of the invention, the sorbent pouches may be constructed so that they cannot easily be opened. In any embodiment of the invention, the sorbent pouches can be completely sealed to form a complete enclosure around the sorbent material. During construction of the sorbent pouch, once the sorbent material is added, the sorbent pouch can be sealed by any possible means. The sorbent pouches can be heat sealed to fuse the edges of the sorbent pouch together. In any embodiment of the invention, an adhesive may be used to connect the edges together. In any embodiment of the invention where a fiber is used to construct the sorbent pouches, the edges may be sewn or woven together to create a sealed sorbent pouch. Any type of chemical or mechanical closure to form the sorbent pouches is contemplated by this invention.

Figure 10A:
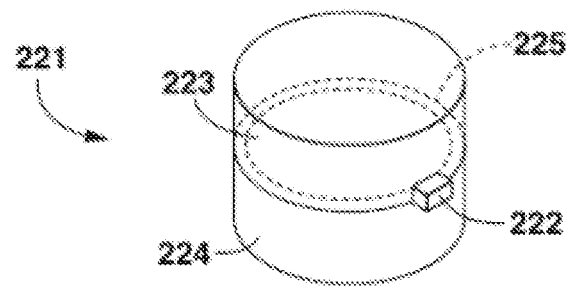
FIG. 10a is a perspective view of a sorbent pouch having an internal sealing ring.
Figure 10B:
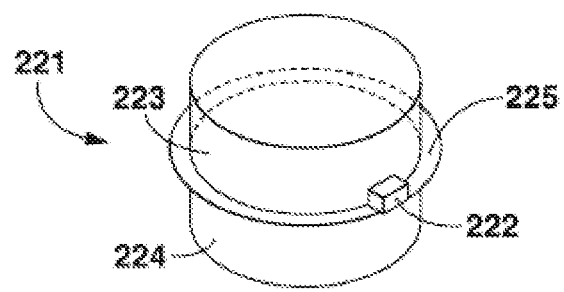
FIG. 10b is a perspective view of a sorbent pouch having an external sealing ring.

In any embodiment of the invention, as shown in FIGS. 10a and 10b, the sorbent pouches may have an interior or exterior ring 225 disposed inside of or around the sorbent pouch 221, respectively, creating an additional sealing member to secure the top portion 223 of the sorbent pouch 221 to the bottom portion 224 of the sorbent pouch 221. The coupled surfaces of the rings may be coated in an adhesive material, or the rings may be attached by any other known coupling means. In any embodiment of the invention, the rings may be welded. In any embodiment of the invention, the rings may be mechanically attached to the sorbent pouches such as with rivets, screws or clamps. In any embodiment of the invention, engagement hooks may be placed on the rings (not shown), wherein the engagement hooks can attach to the sorbent pouch in a similar fashion as described for connecting the top and bottom portions of the sorbent pouches in FIGS. 9a and 9b.

Figure 11:
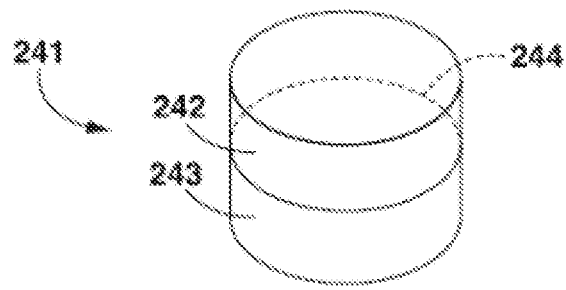
FIG. 11 is a perspective view of a sorbent pouch with an internal separator.

In any embodiment of the invention, such as that shown in FIG. 11, a single sorbent pouch can contain multiple sorbent materials. Sorbent pouch 241 can comprise a separator 244 within the sorbent pouch. The separator 244 can run through the entire interior space of the sorbent pouch 241. The separator 244 creates, within the sorbent pouch 241, a top portion 242 and a bottom portion 243, which are kept completely separate from each other. One sorbent material may be placed in the top portion 242 of the sorbent pouch 241, and a different sorbent material may be placed in the bottom portion 243 of the sorbent pouch 241. This allows two different materials to be placed within a single sorbent pouch, but remain separate from one another. In any embodiment of the invention, two or more sorbent materials can be placed in a single sorbent pouch without a separator. The sorbent materials may be arranged in layers within the sorbent pouch, or may be intermixed. The separator 244 can be constructed from the same material as the sorbent pouch 241 itself, or may be a different material that still allows fluid to pass through the separator 244 freely, while preventing passage of the sorbent material.

In any embodiment of the invention, more than one separator can be used within a single sorbent pouch. The present invention contemplates sorbent pouches containing 2, 3, 4 or more separators within a single sorbent pouch.

In any embodiment of the invention, multiple sorbent materials can be mixed within a sorbent pouch. Mixing different sorbent materials together can be accomplished without a loss in efficiency of the sorbent materials.

Figure 12:
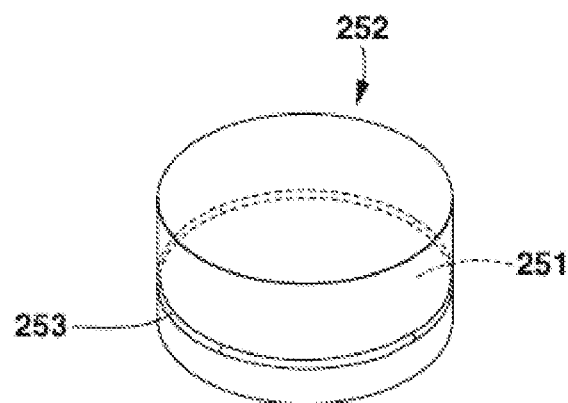
FIG. 12 perspective view of a sorbent pouch in a sorbent cartridge with an o-ring seal member.

The sorbent pouches of the present invention can have a mechanism to create a seal between the sorbent pouch and the inner surface of the sorbent cartridge in which the sorbent pouch is placed, such that fluid is kept from flowing around the sorbent pouch and instead is directed into the sorbent pouch. FIG. 12 shows one non-limiting embodiment of a seal mechanism. A flexible sorbent pouch 251, such as one made out of a fiber, can be placed inside of a sorbent cartridge 252. In any embodiment of the invention, the sorbent pouch may be made out of a rigid material, such as a polymer or metal. In order to avoid a situation in which spent dialysate flows around the sorbent pouch 251 and therefore does not contact the sorbent material inside the sorbent pouch 251, the sorbent pouch 251 may be sealed to the interior surface of the sorbent cartridge 252. O-ring 253 placed on the circumference of sorbent pouch 251 can form a seal with the sorbent cartridge 252 so as to prevent spent dialysate from flowing around the sorbent pouch 251, and instead through the sorbent pouch 251. The sorbent pouch 251 may be filled so that the circumference of the sorbent pouch 251 is slightly wider than that of the sorbent cartridge 252. This will ensure that the sorbent pouch 251 covers the entire inner area of the sorbent cartridge 252 and that there are no spaces for fluid to pass by without flowing through the sorbent pouch 251. O-ring 253 can also serve to ensure that sorbent pouch 251 keeps the intended shape by providing a semi-rigid border.

Figure 13:
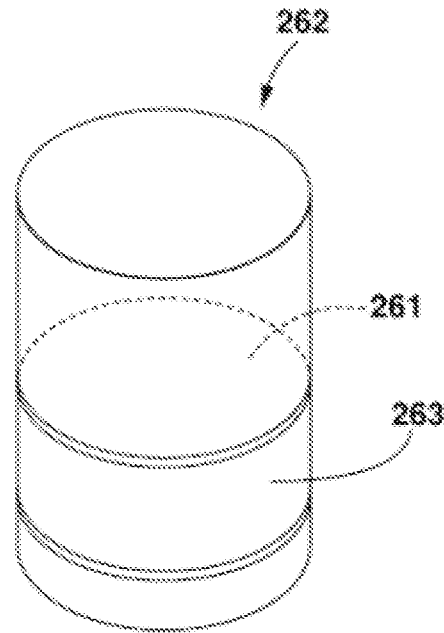
FIG. 13 is a perspective view of a sorbent pouch in a sorbent cartridge with an elastomeric material on the side walls.

In any embodiment of the invention, as shown in FIG. 13, an elastomeric material 263 may be disposed on the edges of the sorbent pouch 261. When the sorbent pouch 261 is placed in the sorbent cartridge 262, the elastomeric material 263 functions like the o-ring described above to create a seal and keep liquid from flowing around the sorbent pouch 261. The elastomeric material 263 can be made to completely cover the outside edges of the sorbent pouch 261, or the elastomeric material can be disposed in one or more thin strips of material. In any embodiment of the invention, the inside walls of the sorbent cartridge 262 may be coated in an elastomeric substance (not shown), which will function to form the same seal when a rigid or semi-rigid sorbent pouch is placed within. In any embodiment of the invention, the sorbent pouches may be constructed to be slightly larger than the sorbent cartridge. When the user inserts the sorbent pouches into the sorbent cartridge, the sorbent pouch can be compressed slightly to fit in the sorbent cartridge. This will ensure that the sorbent pouches cover the entire area inside the sorbent cartridge and facilitate the formation of a seal around the edges of the sorbent pouch.

Figure 14:
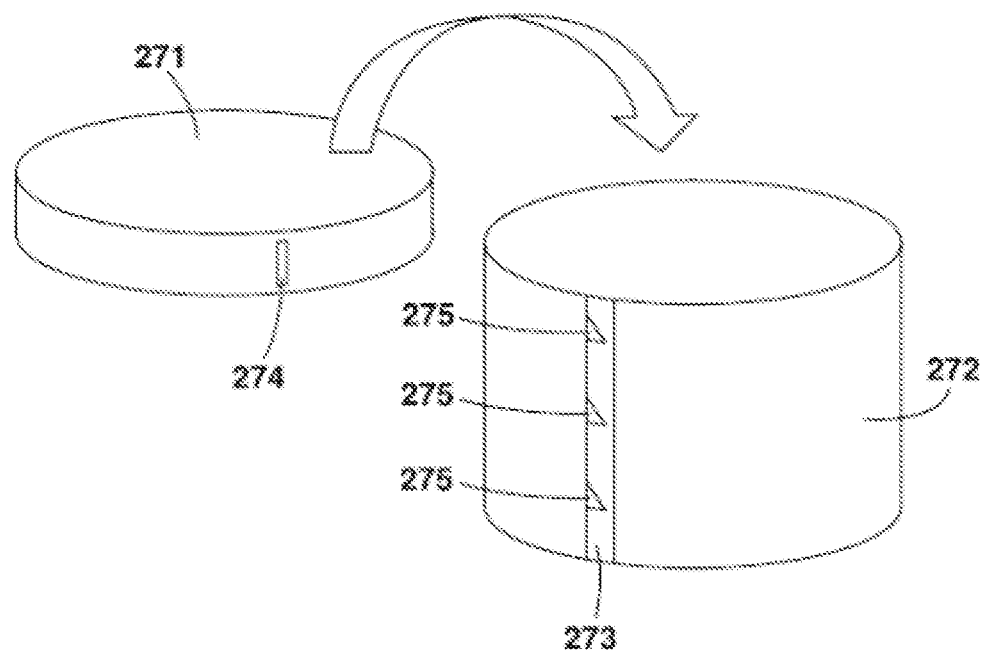
FIG. 14 is a perspective view of a sorbent pouch and cartridge with engagement member to ensure correct alignment.

In any embodiment of the invention, it may be important to ensure that the sorbent pouches are properly inserted into the sorbent cartridge. Any method of doing so is contemplated by this invention. One non-limiting example is shown in FIG. 14. Receiving groove 273 may be created in the wall of the sorbent cartridge 272. A key 274, or flange, may be disposed on the side of the sorbent pouch 271. In order for the sorbent pouch 271 with key 274 to fit within the sorbent cartridge 272, the key 274 must be aligned with groove 273 in the sorbent cartridge 272 wall. This will ensure that the sorbent pouch 271 is disposed within the sorbent cartridge 272 with the correct alignment. In any embodiment of the invention, optional ridges 275 may be placed within groove 273. The ridges 275 can serve to lock the sorbent pouch 271 in place vertically within the sorbent cartridge 272. The ridges 275 may be designed so that they are angled on the top portion of the ridge and flat on the bottom portion of the ridge. Once the key 274 passes a ridge 275 in a downward direction, the ridge 275 can serve to keep the sorbent pouch 271 from inadvertently moving back upward within the sorbent cartridge.

The ridges 275 may be designed such that the sorbent pouch 271 may be removed upward only with the use of force greater than would be expected from inadvertent moving but not so much force as to prevent intentionally lifting the sorbent pouch 271 out of the sorbent cartridge 272. This can be accomplished by using a semi-rigid material as either the key 274, the ridges 275, or both, such that when enough force is applied, the key 274 or ridges 275 can be bent far enough to allow removal of the sorbent pouch 271, after which the key 274 or ridges 275 can return to their original shape. In any embodiment of the invention, the ridges may be attached with a spring mechanism that is connected to a button, such that when the button is depressed the ridges 275 recede into the sorbent cartridge 272 and allow easy removal of the sorbent pouch 271.

In any embodiment of the invention, the sorbent pouches may be loosely contained within the sorbent cartridge. The sorbent pouch need not be made the same size as, or larger than, the sorbent cartridge. One or more sorbent pouches may be constructed of a smaller size than the interior circumference of the sorbent cartridge, and may be simply placed in the sorbent cartridge.

After construction of the sorbent pouch containing a sorbent material or materials, the material within the sorbent pouch can be washed so as to remove any particles smaller than the pore or mesh size of the sorbent pouch material. This will ensure that all particles within the sorbent pouch are large enough so that they cannot inadvertently pass out of the sorbent pouch. Thus, when used in a sorbent cartridge, the sorbent pouches themselves can act as a particulate filter, ensuring that no particulate matter of the sorbent material, or any other particulate matter, can pass downstream. This may eliminate the need for the use of external particulate filters.

In any embodiment of the invention, antimicrobial or antibacterial material may be impregnated into the sorbent pouch. This allows sterilization of the dialysate as the dialysate flows through the sorbent cartridge, and can eliminate the need for antimicrobial filters. In any embodiment of the invention, medication such as heparin or other anticoagulants, or antibiotics may be impregnated into the sorbent pouch. This can allow administration of these medications to the patient without the need for adding the drugs to the dialysate.

Figure 15:
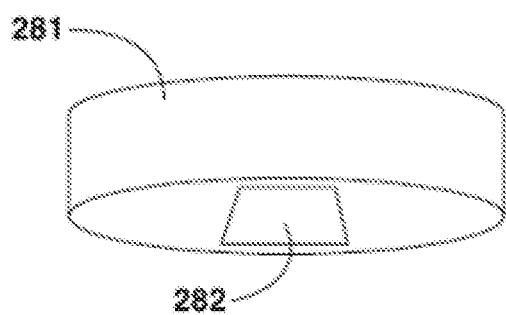
FIG. 15 is a perspective view of a sorbent pouch with a double layer of material in the center to control flow through the sorbent pouch.

In any embodiment of the invention, flow throughout the sorbent pouch can be controlled by variations in the sorbent pouch material. Generally, fluid moving through a conduit will move most quickly through the center of the conduit, and more slowly towards the edges. To ensure that fluid travels more evenly throughout the sorbent pouch, the sorbent pouch can be constructed such that more fluid enters the sorbent pouch on the outer edges of the sorbent pouch than enters in the center. One non-limiting example is shown in FIG. 15. A sorbent pouch 281, such as one made out of a fabric, can be constructed with an extra layer of fabric 282 in the center of the bottom surface of the sorbent pouch 281. This extra layer of fabric 282 effectively reduces the mesh size of the sorbent pouch 281 in that location. With a smaller mesh size, resistance to flow will be greater in the center of the sorbent pouch 281, and fluid flow will be more evenly distributed to the edges of the sorbent pouch 281. In any embodiment of the invention where the sorbent pouch is made out of metal or a polymer, the same effect can be created by making a smaller pore size, or alternatively less pores, in the center of the sorbent pouch. In any embodiment of the invention, a separator, similar to the one shown in FIG. 11 can be utilized in the middle of the sorbent pouch. The separator can be constructed as described above, such as with an extra layer of fabric near the center, to better control the flow of fluid throughout the sorbent pouch. Although shown in FIG. 15 as a centrally positioned rectangular layer, the extra layer of fabric 282 or other material may be positioned anywhere along the outer surface of the sorbent pouch 281, and may take any shape, such as circular, rectangular, triangular, etc.

In any embodiment of the invention, a patterned flow of fluid through the sorbent cartridge can be created. Occlusions, or blockages, of some of the pores can result in restricted flow through some portions of the sorbent pouch. In any embodiment of the invention, some of the pores in the sorbent pouch may be larger or smaller than other pores in the rest of the sorbent pouch. Flow will be increased through the larger pores as compared to the smaller pores, allowing control over fluid flow into and out of the sorbent pouch.

Fluid flows through sorbent materials of varying particle sizes and granular diameters at various rates and pressures. Fluid flows at a higher rate and at a lower pressure through granules of larger diameter, while fluid flows at a slower rate and at a higher pressure through granules of smaller diameter. Wicking can occur when fluid generally flows in the direction of areas of least pressure. For example, fluid flow through a fine particle sorbent material, such as zirconium phosphate, can result in wicking. In such an instance, the fluid has a tendency to flow towards an area of lower resistance, generally near the wall of the container. This can result in the fluid not flowing through a large portion of the sorbent material, such that the fluid is not coming into contact with the sorbent materials. To ensure that fluid flows through the sorbent pouch and the sorbent materials more evenly, the sorbent pouches of the present invention can be constructed such that fluid is directed to flow away from the walls of the sorbent pouch and towards the interior of the sorbent pouch.

Figure 16:
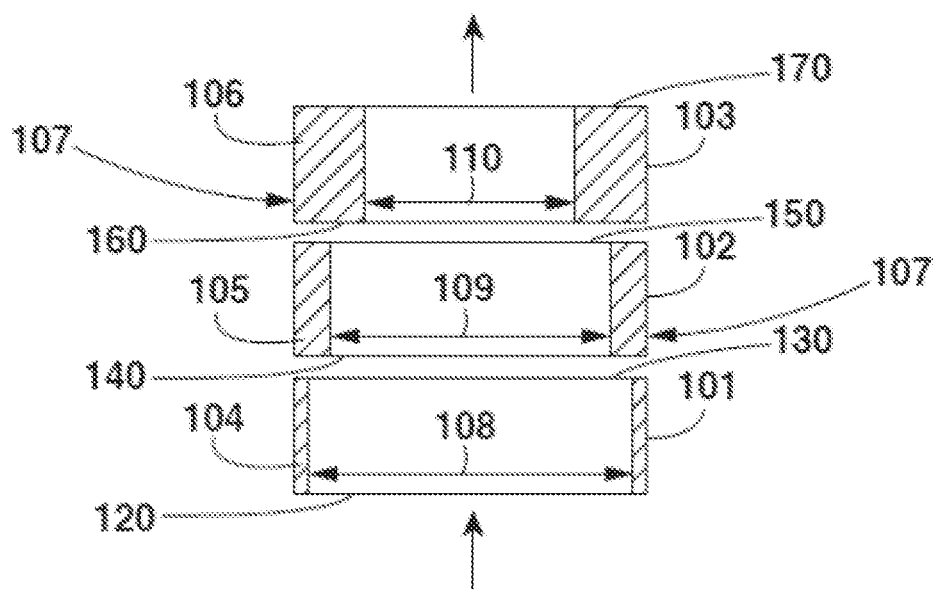
FIG. 16 shows an exploded cross-sectional view of a sorbent cartridge having stacked sorbent pouches, with each sorbent pouch in series having a thicker sidewall, and therefore smaller interior diameter, than that of the previous sorbent pouch in series.

In any embodiment of the invention, flow of fluid through the sorbent pouches can be controlled by varying the interior diameters of the sorbent pouches. In FIG. 16, the second sorbent pouch 102 has an interior wall 105 that is thicker than the interior wall 104 of the first sorbent pouch 101, such that the interior diameter 109 of the second sorbent pouch 102 is smaller than the interior diameter 108 of the first sorbent pouch 101. Similarly, the third sorbent pouch 103 has an interior wall 106 that is thicker than the interior wall 105 of the second sorbent pouch 102, such that the interior diameter 110 of the third sorbent pouch 103 is smaller than the interior diameter 109 of the second sorbent pouch 102. Each sorbent pouch can have a wall that is thicker than that of the immediately preceding sorbent pouch in a direction from the bottom surface 120 of the first sorbent pouch 101 to the top surface 170 of the third sorbent pouch 103 while maintaining a substantially identical outer diameter among each sorbent pouch in sequence. Any number of sorbent pouches can be used in any embodiment of this invention. Fluid flowing through the bottom surface 120 of the first sorbent pouch 101 to the top surface 130 of first sorbent pouch 101, through the bottom surface 140 and top surface 150 of the second sorbent pouch 102, and through the bottom surface 160 to the top surface 170 of the third sorbent pouch 103, is directed into the interior space of each pouch. Because each sorbent pouch has a thicker wall than the preceding sorbent pouch in series, each sorbent pouch has a smaller effective area through which fluid can flow than that of the preceding sorbent pouch. This gradually decreasing flow area will result in pushing the fluid moving from one sorbent pouch to another sorbent pouch along the edges of the sorbent pouches near the wall of the sorbent cartridge 107 towards the center of the subsequent sorbent pouch. In any embodiment of the invention, the wall of each sorbent pouch can be between 5-10% thicker than the wall of the preceding sorbent pouch. In any embodiment of the invention, the thickness of the wall of each sorbent pouch can be between 1-5%, 10-15%, 15-20% or 20-30% thicker than the wall of the preceding sorbent pouch.

Figure 17:
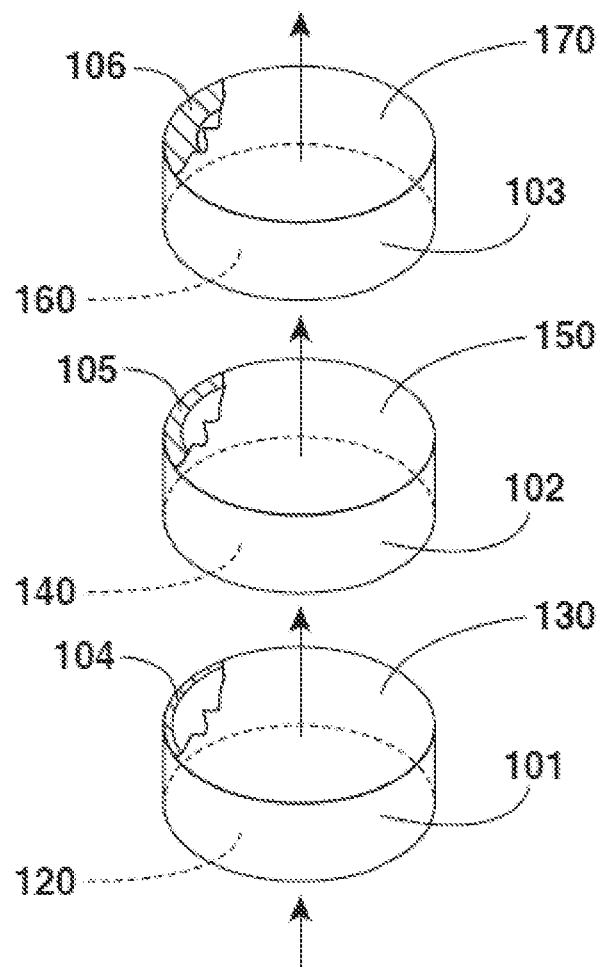
FIG. 17 shows an exploded perspective view of a sorbent cartridge having stacked sorbent pouches, with each sorbent pouch in series having a thicker sidewall, and therefore smaller interior diameter, than that of the previous sorbent pouch

FIG. 17 is an exploded perspective view of FIG. 16. As can be seen, fluid flowing up through the first sorbent pouch 101 through sorbent pouches 102 and 103 will be pushed toward the center of each sorbent pouch by the thickening side walls of each sorbent pouch in series.

Figure 18:
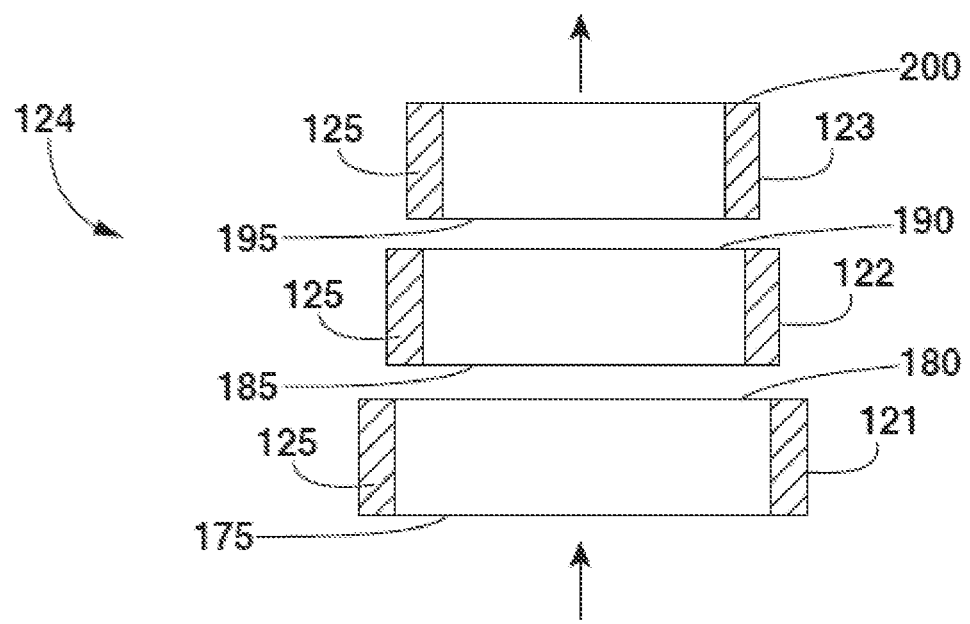
FIG. 18 shows an exploded cross-sectional view of a sorbent cartridge having stacked sorbent pouches, with each sorbent pouch in series having a smaller diameter than that of the previous sorbent pouch.

In any embodiment of the invention, each sorbent pouch may be constructed with a smaller outside diameter than that of the preceding sorbent pouch. Constructing each sorbent pouch with a smaller diameter and the same wall thickness as the previous sorbent pouch will create the same effect as constructing each sorbent pouch with a progressively thicker wall. In any embodiment of the invention, as shown in FIG. 18, the interior diameter of the sorbent cartridge 124 can also decrease for each sorbent pouch. The first sorbent pouch 121 can have the largest diameter of all the sorbent pouches and can be placed in the sorbent cartridge 124 where the interior diameter of the sorbent cartridge 124 is the largest. Second sorbent pouch 122 can have a smaller diameter than that of the first sorbent pouch 121 and can be placed in the sorbent cartridge 124 where the interior diameter of the sorbent cartridge 124 is smaller. Third sorbent pouch 123 can have a smaller diameter than that of the second sorbent pouch 122 and can be placed in the sorbent cartridge 124 where the interior diameter of the sorbent cartridge 124 is smallest. The wall thickness 125 of each sorbent pouches can be constant. In any embodiment of the invention, more than three sorbent pouches can be used, and the sorbent cartridge 124 can have more than three different sized interior diameters. In any embodiment of the invention, fluid can flow up through bottom surface 175 and top surface 180 of first sorbent pouch 121, through bottom surface 185 and top surface 190 of second sorbent pouch 122, and through bottom surface 195 and top surface 200 of third sorbent pouch 123 such that the fluid is passing through a constricting area with each subsequent sorbent pouch in series, and accordingly is pushed toward the center of each sorbent pouch.

Figure 19:
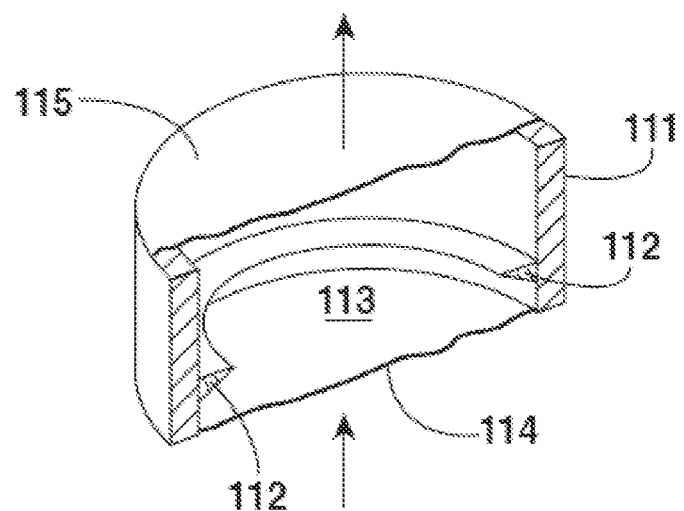
FIG. 19 shows a cross-sectional perspective view of a sorbent pouch having an annular ring disposed on the interior circumference of the sorbent pouch.

In any embodiment of the invention, as shown in FIG. 19, annular rings or "o-rings" may be used to direct flow of fluid into the center of the sorbent pouch. A sorbent pouch 111 can have an annular ring 112 placed and adhered by any known means around the interior circumference of the sorbent pouch 111. The cross-section of the annular ring 112 can be angled so that the annular ring 112 extends radially into the interior 113 of the sorbent pouch 111. The angle of the annular ring 112 can direct fluid entering the bottom surface 114 of the sorbent pouch 111 from the area near the edge of the sorbent pouch 111 into the interior 113 of the sorbent pouch 111 as the fluid exits through the top surface 115 of the sorbent pouch 111. In any embodiment of the invention, the annular ring can have a curved shape. In any embodiment of the invention, the annular ring can have a rectangular shape. In any embodiment of the invention, each sorbent pouch can include multiple annular rings. For example, a sorbent pouch may have 2, 3, 4, 5, 6 or more annular rings spaced along the interior circumference of the sorbent pouch to continuously push fluid into the center of the sorbent pouch as the fluid passes through the sorbent pouch. The annular rings may be made out of any substance known in the art. In any embodiment of the invention, the annular rings may be constructed from an elastomeric material, such as the o-rings described above. In any embodiment of the invention, the annular rings may be constructed from plastic or some other inert material. In any embodiment of the invention, the annular rings may extend inwardly towards the center of the sorbent pouch at a length of between 5-10% of the diameter of the sorbent pouch. In any embodiment of the invention, the annular rings may extend between 1-5%, 10-15%, 15-20% or 20-30% of the diameter of the sorbent pouch.

One skilled in the art will understand that various combinations and/or modifications and variations can be made in the stacked sorbent assembly depending upon the specific needs for operation. Moreover, features illustrated or described as being part of the invention can be included in the invention, either alone or in combination.

We claim:

1. A sorbent assembly, comprising:
   two or more sorbent pouches stacked in series; the two or more sorbent pouches formed from a porous material wherein the sorbent pouches contain at least one sorbent material and the porous material allows fluid to pass through the sorbent pouches;
   wherein at least a first of the two or more sorbent pouches contains solid urease, and wherein the porous material retains at least 98% by weight of the solid urease in the first sorbent pouch;
   wherein the porous material allows dissolved urease to pass through the sorbent pouch.

2. The sorbent assembly of claim 1, wherein a second sorbent pouch of the two or more sorbent pouches contains alumina.

3. The sorbent assembly of claim 1, further comprising zirconium phosphate in the sorbent assembly downstream of the first sorbent pouch.

4. The sorbent assembly of claim 1, wherein a second sorbent pouch of the two or more sorbent pouches contains one or more sorbent materials selected from the group consisting of activated carbon, zirconium phosphate, and zirconium oxide.

5. The sorbent assembly of claim 1, wherein a second sorbent pouch of the two or more sorbent pouches contains zirconium phosphate; and wherein the second sorbent pouch is downstream of the first sorbent pouch.

6. The sorbent assembly of claim 1, wherein the sorbent assembly is contained within a sorbent assembly shell, and wherein the two or more sorbent pouches are detachable from the sorbent assembly shell.

7. The sorbent assembly of claim 1, wherein the first sorbent pouch has a first engagement member; wherein a second sorbent pouch of the two or more sorbent pouches has a second engagement member; the first sorbent pouch connecting to the second sorbent pouch by connecting the first engagement member to the second engagement member.

8. The sorbent assembly of claim 1, the two or more sorbent pouches including at least a second sorbent pouch containing activated carbon, a third sorbent pouch containing zirconium oxide, and a fourth sorbent pouch containing zirconium phosphate.

9. The sorbent assembly of claim 1, further comprising at least one sensor in fluid communication with fluid flowing out from at least one of the sorbent pouches, the sensor being capable of sensing the presence and/or concentration of at least one compound in the fluid.

10. The sorbent assembly of claim 9, wherein the at least one sensor comprises a urea sensor and/or an ammonia sensor.

11. A system, comprising:
the sorbent assembly of claim 1, further comprising a second sorbent pouch containing alumina; and
an injector fluidly connected to a flow path containing the sorbent assembly;
the injector configured to inject a urease solution into the flow path upstream of the sorbent assembly allowing the urease in solution to bind to the alumina contained in the second sorbent pouch.

12. The system of claim 11, wherein the injector is upstream of the sorbent assembly.

13. The system of claim 11, further comprising at least a third sorbent pouch; the second sorbent pouch containing one or more sorbent materials selected from the group consisting of activated carbon, zirconium phosphate, and zirconium oxide.

14. The system of claim 13, wherein the third sorbent pouch contains zirconium phosphate and wherein the third sorbent pouch is downstream of the sorbent pouch containing alumina.

15. The system of claim 13, wherein the first sorbent pouch has a first engagement member; wherein a second sorbent pouch of the two or more sorbent pouches has a second engagement member; the first sorbent pouch connecting to the second sorbent pouch by connecting the first engagement member to the second engagement member.

16. The system of claim 11, further comprising zirconium phosphate in the sorbent assembly downstream of the alumina.

17. The system of claim 11, wherein the sorbent assembly is contained within a sorbent assembly shell, and wherein the sorbent pouch containing alumina is detachable from the sorbent assembly shell.

18. The system of claim 11, further comprising at least one sensor in fluid communication with fluid flowing out from at least one sorbent pouch, the sensor being capable of sensing the presence and/or concentration of at least one compound in the fluid.

19. The system of claim 18, wherein the at least one sensor comprises a urea sensor and/or an ammonia sensor.

* * * * *